United States Patent
O'Mahony

(12) 
(10) Patent No.: US 6,521,737 B1
(45) Date of Patent: Feb. 18, 2003

(54) PEPTIDES WHICH ENHANCE TRANSPORT ACROSS TISSUES AND METHODS OF IDENTIFYING AND USING THE SAME

(75) Inventor: Daniel Joseph O'Mahony, Dublin (IE)

(73) Assignee: Elan Corporation, plc, Dublin (IE)

( * ) Notice: Subject to any disclaimer, the term of this patent is extended or adjusted under 35 U.S.C. 154(b) by 0 days.

(21) Appl. No.: 09/573,252

(22) Filed: May 18, 2000

Related U.S. Application Data

(62) Division of application No. 08/746,411, filed on Nov. 8, 1996, now Pat. No. 6,117,632.
(60) Provisional application No. 60/006,461, filed on Nov. 10, 1995.

(30) Foreign Application Priority Data

Nov. 10, 1995 (IE) ................................................ 950865

(51) Int. Cl.[7] .............................................. C07K 14/00
(52) U.S. Cl. ....................................... 530/300; 530/350
(58) Field of Search .............................. 435/5, 6, 91.2, 435/91.1, 68.1; 530/300, 350

(56) References Cited

U.S. PATENT DOCUMENTS 5,672,584 A * 9/1997 Borchardt et al. ............. 435/6

* cited by examiner

*Primary Examiner*—Kenneth R. Horlick
(74) *Attorney, Agent, or Firm*—Synnestvedt & Lechner LLP

(57) ABSTRACT

A method of identifying a peptide which permits or facilitates the transport of an active agent through a human or animal tissue. A predetermined amount of phage from a random phage library or preselected phage library is plated unto or brought into contact with a first side, preferably the apical side, of a tissue sample or polarized tissue cell culture. At a predetermined time, the phage which is transported to a second side of the tissue opposite the first side, preferably the basolateral side, is harvested to select transported phage. This modified phage is amplified in a host. This cycle of events is repeated (using the transported phage produced in the most recent cycle) a predetermined number of times to obtain a selected phage library containing phage which can be transported from the first side to the second side. Lastly, the identity of at least one peptide coded by phage in the selected phage library is determined to identify a peptide which permits or facilitates the transport of an active agent through a human or animal tissue.

6 Claims, 5 Drawing Sheets

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "gene VIII primer ELN 71"

(xi) SEQUENCE DESCRIPTION: SEQ ID NO: 1:

AGTAGCAGAA GCCTGAAGA                                        19

(2) INFORMATION FOR SEQ ID NO: 2:

(i) SEQUENCE CHARACTERISTICS:
      (A) LENGTH: 179 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Class of 9 Clones"

(xi) SEQUENCE DESCRIPTION: SEQ ID NO: 2:

AAGCTTTGCC GTTTGCGCCT TGTGGTTATA AGCATCCTAC TTGTCGTGTG GAGCCTGCAG    60

ACGCCACATA ATAAACAGCG GCGCAGTATA ACCCCAAGGC GGAATGCTGC AGGGACGTTG    120

GCAAAGCTTT CCGGTTTCGG CTCGGATTTA TTATGGGTAT GCATGATTCT CCTGATCCT     179

(2) INFORMATION FOR SEQ ID NO: 3:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Class of 5 clone"

(xi) SEQUENCE DESCRIPTION: SEQ ID NO: 3:

AAGCTTTGCC CTTACTAGCA GATGCCTGAG CTGTATTCTC CTCATCGTTT TTGTCCTGCA    60

GATATACGCC ATATACAGCG GATAAGTAAA AATAGTAGGA GTAAGCAAAG CTTTGCCCTC    120

GTCAGCTGTA TCCTGCGCCG CCGACTGAGC TTACTGTGCG TC                      162

(2) INFORMATION FOR SEQ ID NO: 4:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Class of 3 clones"

(xi) SEQUENCE DESCRIPTION: SEQ ID NO: 4:

AAGCTTTGCC TGCGTAGGCC TATTCCTTCT TTGCTGCCGG TGCCACTTGT ATCGCTGCAG    60

GCTTAGTATA GAGGCCCAAA AATAGGAGAA GGCACCAGAT ATAGATGCAG GACGTTGGCA    120

AACTTTGCGG CTGTCTAACC GATTGTTCGG CCTCTGCATT TGTACTGGTC               170

(2) INFORMATION FOR SEQ ID NO: 5:

(i) SEQUENCE CHARACTERISTICS:
        (A) LENGTH: 158 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Individual isolate"

(xi) SEQUENCE DESCRIPTION: SEQ ID NO: 5:

TCGCATTCTC CGGGCCTTTT GCGAATTTTC GGCAATGGTT GCGTCCTGCA GGAAACCCAA    60

ACGCCCACAA ACACGCAGAA GACGCCGGAG AAAAAGTGCA AAGCTTTGCC ATTTTGCTGC    120

CTAGGATTCC GCATCCGTTT GTGTCCGGCT CCTTTGTC                           158

(2) INFORMATION FOR SEQ ID NO: 6:

(i) SEQUENCE CHARACTERISTICS:
        (A) LENGTH: 163 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "individual isolate"

(xi) SEQUENCE DESCRIPTION: SEQ ID NO: 6:

```
GGGCTTCGGG TTACTTGTAC TCGGCGTCCT CCTCTTTGTC CTGCAGGCAA ATAAGGCTGC      60

TGACACCTAG TAGTGCGAAG ACAGCCTCTG CAGGGAAGTT GGCAAAGCTT TGCCGGGCCG     120

ATTTCAGGTG TTCCTCTTGA TGTTTTTTGC TTTTTGGGTT GTC                      163
```

(2) INFORMATION FOR SEQ ID NO: 7:

(i) SEQUENCE CHARACTERISTICS:
        (A) LENGTH: 141 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "individual isolate"

(xi) SEQUENCE DESCRIPTION: SEQ ID NO: 7:

```
CTCAGCCTTA TTAGGTGCCT TGGATCCTCT GGTCGCCTAT GCCTGCAGCA AGCAGTAGTA      60

TACCATAGTA GAGGCAGAGT CTACATGCAA AGCTTTGCCT CCTATGTTAG AGTCCGGATA     120

GTGGGTCTTT GTCGGAGTCC C                                               141
```

(2) INFORMATION FOR SEQ ID NO: 8:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "individual isolate"

(xi) SEQUENCE DESCRIPTION: SEQ ID NO: 8:

```
TTGGTTGGTT ATCGGCTCAG CGTCTCTGCA GCCGCAAGTC GAAACGCGAC CACGAAGTCA      60

GATACTCCAA AAAGCAAAGC TTTGCCTGTC AGTCGCCTAG GTAGCGTGCT TCTCGGTCTC     120

TGCGGCCTC                                                             129
```

(2) INFORMATION FOR SEQ ID NO: 9:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "individual isolate"

(xi) SEQUENCE DESCRIPTION: SEQ ID NO: 9:

```
TCTACGCAGT TCCGTTGTGG GTGTCTTGTT CCTCCTACTC CTCCTGCAGG AAAAGAACAC      60

TCCAGCACGA TGAGGAATCT CCTAAAAAAT AGTCTGCAGG AGTTGCAAAG CTTTGCCTTG     120

TTGCCG                                                                126
```

(2) INFORMATION FOR SEQ ID NO: 10:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "individual isolate"

(xi) SEQUENCE DESCRIPTION: SEQ ID NO: 10:

```
GTTAGACGGT GCAGGCGCCT ATTAATCAGC CTGAGGATTG GCCTC                                45
```

(2) INFORMATION FOR SEQ ID NO: 11:

(i) SEQUENCE CHARACTERISTICS:
        (A) LENGTH: 118 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 2..103

(xi) SEQUENCE DESCRIPTION: SEQ ID NO: 11:

```
T GCA GAT GAT TTT ATG CAG TGC ATG CTA ACT TTG CCA ACG TCC CTG            46
  Ala Asp Asp Phe Met Gln Cys Met Leu Thr Leu Pro Thr Ser Leu
   1               5                  10                  15

CAG CAG GAG CAG TCT CCC TAT AAT TAC TAC GAC ACC CAT GAA GCG AAT          94
Gln Gln Glu Gln Ser Pro Tyr Asn Tyr Tyr Asp Thr His Glu Ala Asn
                 20                  25                  30

CAA CCT CAC GCTGCAGAAG GTGAT                                            118
Gln Pro His
```

(2) INFORMATION FOR SEQ ID NO: 12:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO: 12:

```
Ala Asp Asp Phe Met Gln Cys Met Leu Thr Leu Pro Thr Ser Leu Gln
 1               5                  10                  15

Gln Glu Gln Ser Pro Tyr Asn Tyr Tyr Asp Thr His Glu Ala Asn Gln
             20                  25                  30

Pro His
```

(2) INFORMATION FOR SEQ ID NO: 13:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 16..105

(xi) SEQUENCE DESCRIPTION: SEQ ID NO: 13:

```
ATGCTATCGT TTGCC ACG CCG ACG ACG ACC GCT ACC GTA GTA GGG ACG ACT         51
                 Thr Pro Thr Thr Thr Ala Thr Val Val Gly Thr Thr
                                  35                  40                  45

CAG CCT GTT GAT TTG TCT AGT AAG CAT CTG CTT AGG CAT CCT TGT CGT          99
Gln Pro Val Asp Leu Ser Ser Lys His Leu Leu Arg His Pro Cys Arg
                 50                  55                  60

GAG TTT GCTGCAGAAG GTGAT                                                120
Glu Phe
```

(2) INFORMATION FOR SEQ ID NO: 14:

(i) SEQUENCE CHARACTERISTICS:
        (A) LENGTH: 30 amino acids
        (B) TYPE: amino acid
        (D) TOPOLOGY: linear (ii) MOLECULE TYPE: protein (xi) SEQUENCE DESCRIPTION: SEQ ID NO: 14:

```
Thr Pro Thr Thr Thr Ala Thr Val Val Gly Thr Thr Gln Pro Val Asp
 1               5                  10                  15

Leu Ser Ser Lys His Leu Leu Arg His Pro Cys Arg Glu Phe
            20                  25                  30
```

(2) INFORMATION FOR SEQ ID NO: 15:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 16..105

(ix) FEATURE:
        (A) NAME/KEY: -
        (B) LOCATION: 31..33
        (D) OTHER INFORMATION: /product= "GLN"
            /label= GLN
            /note= "Amber suppressor SupE in E. coli strain K91Kan
            reads in-frame stop codons TAG as GLN residues"

(ix) FEATURE:
        (A) NAME/KEY: -
        (B) LOCATION: 43..45
        (D) OTHER INFORMATION: /product= "GLN"
            /label= GLN
            /note= "Amber suppressor SupE in E.coli strain K91Kan
            reads in-frame stop codon TAG as GLN residues"

(xi) SEQUENCE DESCRIPTION: SEQ ID NO: 15:

```
ATGCTATCGT TTGCC ATG TCG CCT GAT CAT TAG TAT GCG CTT TAG TCG TCC         51
                 Met Ser Pro Asp His Gln Tyr Ala Leu Gln Ser Ser
                                      35                  40

TTT GTC TTG CCG TGT TGT CGG CCT CTT CTG GTT GAT TCT GAT TAT ATT         99
Phe Val Leu Pro Cys Cys Arg Pro Leu Leu Val Asp Ser Asp Tyr Ile
             45                  50                  55

CAT TCT GCTGCAGAAG GTGAT                                                120
His Ser
    60
```

(2) INFORMATION FOR SEQ ID NO: 16:

(i) SEQUENCE CHARACTERISTICS:
        (A) LENGTH: 30 amino acids
        (B) TYPE: amino acid
        (D) TOPOLOGY: linear (ii) MOLECULE TYPE: protein (xi) SEQUENCE DESCRIPTION: SEQ ID NO: 16:

```
Met Ser Pro Asp His Gln Tyr Ala Leu Gln Ser Ser Phe Val Leu Pro
 1               5                  10                  15

Cys Cys Arg Pro Leu Leu Val Asp Ser Asp Tyr Ile His Ser
```

-continued

```
                    20                  25                  30

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "geneIII primer ELN77a"

(xi) SEQUENCE DESCRIPTION: SEQ ID NO: 17:

CCCTCATAGT TAGCGTAACG                                                  20
```

US 6,521,737 B1

PEPTIDES WHICH ENHANCE TRANSPORT ACROSS TISSUES AND METHODS OF IDENTIFYING AND USING THE SAME

This application is a division, of application Ser. No. 08/746,411, filed Nov. 8, 1996, U.S. Pat. No. 6,117,632, which claims benefit of U.S. provisional application No. 60/006,461 filed Nov. 10, 1995.

FIELD OF THE INVENTION

This invention relates to the identification of peptide sequences which permit or facilitate the transport of drugs, macromolecules, or particles, such as biodegradable nano- and microparticles, through human or animal tissues. In particular, this invention relates to the use of phage display libraries in a screening assay in order to determine the identity of peptides sequences which enhance the delivery of the bacteriophage through tissue, such as epithelial cells lining the lumenal side of the gastrointestinal tract (GIT).

BACKGROUND OF THE INVENTION

The epithelial cells lining the lumenal side of the GIT are a major barrier to drug delivery following oral administration. However, there are four recognized transport pathways which can be exploited to facilitate drug delivery and transport: the transcellular, paracellular, carrier-mediated and transcytotic transport pathways. The ability of a conventional drug, peptide, protein, macromolecule or nano- or microparticulate system to "interact" with one of these transport pathways may result in increased delivery of that drug or particle from the GIT to the underlying circulation.

In the case of the receptor-mediated, carrier-mediated or transcytotic transport pathways, some of the "uptake" signals have been identified. These signals include, inter alia, folic acid, which interacts with the folate receptor, mannose and cetylmannoside, which interact with the mannose receptor, and cobalamin, which interacts with Intrinsic Factor. In addition, leucine- and tyrosine-based peptide sorting motifs or internalization sequences exist, such as YSKV, FPHL, YRGV, YQTI, TEQF, TEVM, TSAF, YTRF, which facilitate uptake or targeting of proteins from the plasma membrane to endosomes. Phage display libraries can be screened using specific membrane receptors or binding sites to identify peptides that bind specifically to the receptor or binding site. The ability of certain motifs or domains of peptides or proteins to interact with specific membrane receptors, followed by cellular uptake of the protein:receptor complex may point towards the potential application of such motifs in facilitating the delivery of drugs. However, the identification of peptides or peptide motifs by their ability to interact with specific receptor sites or carrier sites, such as sites expressed on the apical side of the epithelial sites of the GIT, may not be able to determine, or may not be the most effective way to determine, the identity of peptides capable of enhancing the transport of an active agent, especially a drug-loaded nano- or microparticle, through tissues such as epithelial lining.

Non-receptor-based assays to discover particular ligands have also been used. For instance, a strategy for identifying peptides that alter cellular function by scanning whole cells with phage display libraries is disclosed in Fong et al., *Drug Development Research* 33:64–70 (1994). However, because whole cells, rather than intact tissue or polarized cell cultures, are used for screening phage display libraries, this procedure does not provide information regarding sequences whose primary function includes affecting transport across polarized cell layers.

Additionally, Stevenson et al., *Pharmaceutical Res.* 12(9), S94 (1995) discloses the use of Caco-2 monolayers to screen a synthetic tripeptide combinatorial library for information relating to the permeability of di- and tri-peptides. While useful, this technique does not assess the ability of the disclosed di- and tri-peptides to enhance delivery of a drug, especially a drug-loaded nano- or microparticle formulation.

Thus, there exists a need for a method of determining peptide sequences that are particularly effective in transporting drugs, including drug-loaded nano- and microparticles, across a human or animal tissue barrier.

SUMMARY OF THE INVENTION

The invention provides a method of identifying a peptide which permits or facilitates the transport of an active agent through a human or animal tissue. A predetermined amount of phage from a random phage library is plated unto or brought into contact with a first side, preferably the apical side, of a tissue sample, either in vitro, in vivo or in situ, or polarized tissue cell culture. At a predetermined time, the phage which is transported to a second side of the tissue opposite the first side, preferably the basolateral side, is harvested to select transported phages. The transported phages are amplified in a host and this cycle of events is repeated (using the transported phages produced in the most recent cycle) a predetermined number of times, such as from zero to six times, to obtain a selected phage library containing phage which can be transported from the first side to the second side. Lastly, the sequence of at least one random peptide coded by phage in the selected phage library is determined in order to identify a peptide which permits or facilitates the transport of an active agent through a human or animal tissue. The transported phage can be viewed as a combination of a transporter peptide (the at least one random peptide coded by the phage) associated with an active agent payload (the phage) in which the transporter peptide facilitates the transport of the active agent through the tissue. Thus, the random peptides coded by phage in the selected phage library are predictively capable of facilitating transport of other active agents, such as drug encapsulated nano- and/or microparticles, through the particular tissue.

Preferably, the tissue sample derives from the duodenum, jejunum, ileum, ascending colon, transverse colon, descending colon, pelvic colon, vascular endothelium cells which line the vascular system, vascular endothelial cells which form the blood brain barrier, alveolar cells, liver, kidney, bone marrow, retinal cells of the eye or neuronal tissue. The tissue sample can be either in vitro or in vivo More preferably, the tissue sample comprises epithelial cells lining the lumenal side of the GIT, such as isolated rat colon or small intestine segments or epithelial cells lining the lumenal side of the GIT found in an open or closed loop animal model system. Other preferred tissue samples are heart, spleen, pancrease, thymus and brain tissue.

Preferably, the polarized tissue cell culture sample is cultured from GIT epithelial cells, alveolar cells, endothelial cells of the blood-brain barrier, or vascular smooth muscle cells. More preferably, the polarized tissue cell culture sample is a polarized Caco-2 cell culture or a polarized T-84 cell culture.

Preferably, the active agent is a drug or a nano- or microparticle. More preferably, the active agent is a drug encapsulated or drug loaded nano- or microparticle, such as a biodegradable nano- or microparticle, in which the peptide is physically adsorbed or coated or covalently bonded, such as directly linked or linked via a linking moiety, onto the surface of the nano- or microparticle. Alternatively, the peptide can form the nano- or microparticle itself or can be directly conjugated to the active agent. Such conjugations include fusion proteins in which a DNA sequence coding for the peptide is fused in-frame to the gene or cDNA coding for a therapeutic peptide or protein, such that the modified gene codes for a recombinant fusion protein in which the "targeting" peptide is fused to the therapeutic peptide or protein and where the "targeting" peptide increases the absoption of the fusion protein from the GIT.

DETAILED DESCRIPTION OF THE INVENTION

Figure 1:
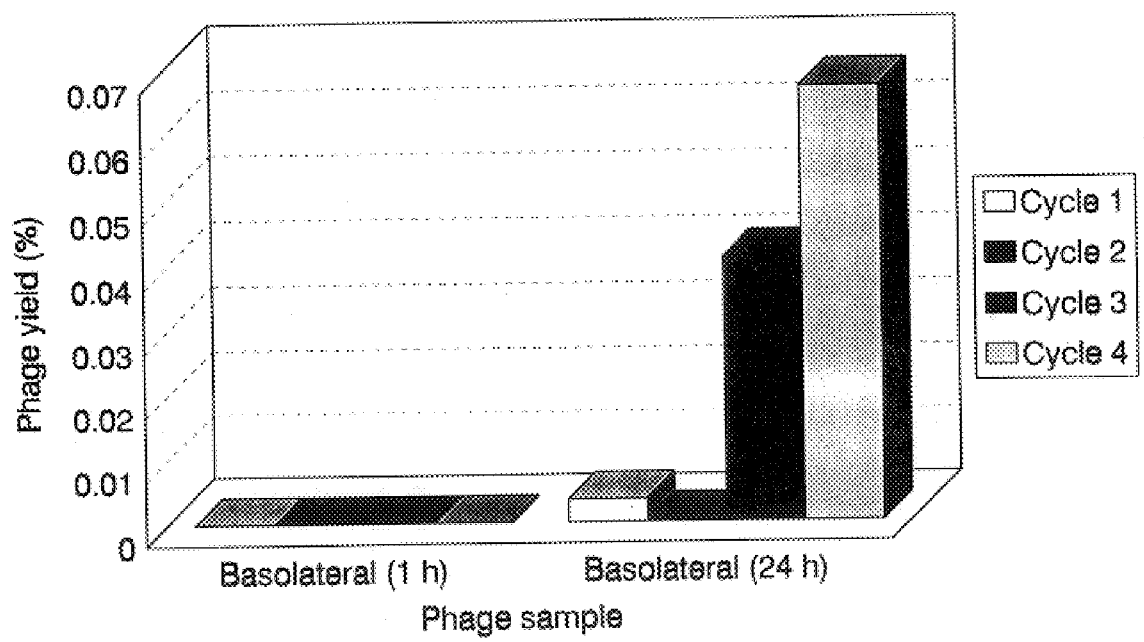
FIG. 1 shows the phage yield (% phage transported from the apical to basolateral medium) in the basolateral medium of polarized Caco-2 cells grown on snapwells at cycles 1, 2, 3, and 4 of panning of the X30 phage display library. For each cycle, the basolateral medium was sampled both 1 hour and 24 hours post addition of phage to the apical medium.

Surprisingly, this invention discloses a method of identifying peptides that are capable of facilitating the delivery or transport of an active agent such as a drug across human or animal tissues, including without limitation GIT epithelial layers, alveolar cells, endothelial cells of the blood-brain barrier, vascular smooth muscle cells, vascular endothelial cells, renal epithelial cells, M cells of the Peyers Patch, and hepatocytes. Furthermore, delivery systems, e.g., nanoparticles, microparticles, liposomes, micelles, could be coated externally with, be linked to or be comprised of these "homing" peptides to permit targeted delivery of encapsulated drugs across particular tissues. In addition, fusion proteins can be synthesized, either in vivo or in vitro, whereby the peptide is fused in-frame to a therapeutic peptide or protein active agent such that the peptide enhances the delivery or transport of the therapeutic peptide or protein across the tissue.

As used herein, the term human or animal "tissue" includes, without limitation, the duodenum, jejunum, ileum, ascending colon, transverse colon, descending colon, pelvic colon, the vascular endothelium which line the vascular system, the vascular endothelial cells which form the blood brain barrier, vascular smooth muscle, alveolar, liver, kidney, bone marrow, heart, spleen, pancreas, thymus, brain, spinal, neuronal and retinal eye tissue.

As used herein, the term "polarized tissue cell culture" refers to cells cultured so as to form polarized cell layers including, without limitation, cell cultures derived from GIT epithelial cells, alveolar cells, endothelial cells of the blood-brain barrier, or vascular smooth muscle cells or any other cell type which upon tissue culturing becomes polarized or adopts morphological characteristics or (topological) structures or appendages specific to that cell type in vivo.

As used herein, the term "active agent" includes, without limitation, any drug or antigen or any drug- or antigen-loaded or drug- or antigen-encapsulated nanoparticle, microparticle, liposome, or micellar formulation capable of eliciting a biological response in a human or animal. Examples of drug- or antigen-loaded or drug- or antigen-encapsulated formulations include those in which the active agent is encapsulated or loaded into nano- or microparticles, such as biodegradable nano- or microparticles, and which have the peptide adsorbed, coated or covalently bonded, such as directly linked or linked via a linking moiety, onto the surface of the nano- or microparticle. Additionally, the peptide can form the nano- or microparticle itself or the peptide can be covalently attached to the polymer or polymers used in the production of the biodegradable nano- or microparticles or drug-loaded or drug-encapsulated nano- or microparticles or the peptide can be directly conjugated to the active agent. Such conjugations to active agents include fusion proteins in which a DNA sequence coding for the peptide is fused in-frame to the gene or cDNA coding for a therapeutic peptide or protein such that the modified gene codes for a recombinant fusion protein.

As used herein, the term "drug" includes, without limitation, any pharmaceutically active agent. Representative drugs include, but are not limited to, peptides or proteins, hormones, analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, anti-neoplastics, prostaglandins and. antidiuretic agents. Typical drugs include peptides, proteins or hormones such as insulin, calcitonin, calcitonin gene regulating protein, atrial natriuretic protein, colony stimulating factor, betaseron, erythropoietin (EPO), interferons such as α, β, or γ interferon, somatropin, somatotropin, somatostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues thereof; analgesics such as fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogues thereof; anti-migraine agents such as sumatriptan, ergot alkaloids, and analogues thereof; anti-coagulant agents such as heparin, hirudin, and analogues thereof; anti-emetic agents such as scopolamine, ondansetron, domperidone, metoclopramide, and analogues thereof; cardiovascular agents, anti-hypertensive agents and vasodilators such as diltiazem, clonidine, nifedipine, verapamil, isosorbide-5-mononitrate, organic nitrates, agents used in treatment of heart disorders, and analogues thereof; sedatives such as benzodiazepines, phenothiozines, and analogues thereof; narcotic antagonists such as naltrexone, naloxone, and analogues thereof; chelating agents such as deferoxamine, and analogues thereof; anti-diuretic agents such as desmopressin, vasopressin, and analogues thereof; anti-anginal agents such as nitroglycerine, and analogues thereof; anti-neoplastics such as 5-fluorouracil, bleomycin, and analogues thereof; prostaglandins and analogues thereof; and chemotherapy agents such as vincristine, and analogues thereof Representative drugs also include antisense oligonucleotides, genes, gene correcting hybrid oligonucleotides, ribozymes, aptameric oligonucleotides, triple-helix froming oligonucleotides, inhibitors of signal transduction pathways, tyrosine kinase inhibitors and DNA modifying agents. As used herein, the term "drug" also includes, without limitation, systems for gene delivery and gene therapeutics, including viral systems for gene delivery such as adenovirus, adeono-associated virus, retroviruses, herpes simplex virus, sindbus virus, liposomes, cationic lipids, dendrimers, imaging agents and enzymes.

As used herein, the term "preselected phage library" refers to library consisting of a subpopulation of a phage display library. This subpopulation is formed by initially screening against either a target molecule, such as a protein, receptor, enzyme, ion channel, kinase, growth factor or growth factor receptor so as to permit the selection of a subpopulation of phages which specifically bind to the target molecule. Alternatively, the subpopulation can be formed by screening against a target cell or cell type or tissue type, gastro-intestinal track, blood brain barrier or other tissue or tissue barrier so as to permit the selection of a subpopulation of phages which either bind specifically to the target cell or target cell type or target tissue or target tissue barrier, or which binds to and/or is transported across (or between) the target cell, target cell type or target tissue or target tissue barrier either in situ or in vivo. This preselected phage library or subpopulation of selected phages can also be rescreened against the target molecule or cell or tissue, permitting the further selection of a subpopulation of phages which bind to the target molecule or target cell, target tissue or target tissue barrier or which bind to and/or is transported across the target cell, target tissue or target tissue barrier either in situ or in vivo. Such rescreening can be repeated from zero to 30 times with each successive "pre-selected phage library," generating additional pre-selected phage libraries.

As used herein, the phrase "human or animal tissue" refers to animal tissue explicitly including human tissue.

It has previously been shown that the $NH_2$-terminal amino acid sequence of the absorption proteins pIII and pVIII coded by *Escherichia coli* filementous bacteriophage phage such as fd, can be modified by recombinant DNA technology to include a library of random peptide sequences of defined length (Cwirla et al., *Proc. Natl. Acad. Sci. USA* 87:6378–6382 (1990)). Thus, a DNA library of modified phage fd sequences, coding for variable pill or pVIII proteins can be constructed and propagated in *E. coli*.

This invention discloses the use of phage display libraries such as these in a random screening approach or a preselected phage library or subpopulation from a phage display library in a preselected screening approach in order to determine the identity of peptide sequences which enhance the delivery of the bacteriophage from either the apical to basolateral side or the basolateral to apical side of either cultured model systems or in in vitro, in situ or in vivo tissue samples. Peptides that enhance the delivery from the apical to basolateral side (e.g., gut side to blood side) can be used to enhance the delivery of active agents in that direction. The converse holds for peptides that enhance the delivery from the basolateral to the apical side. For instance, plating on the basolateral side might determine peptides useful for raising a mucosal immune response to an antigen administered IV, subcutaneously, transdermally or by the opthalmic route.

The size of the random peptide sequences coded by the libraries can be of any size. The libraries can be designed to code for linear peptides. Alternatively, the libraries can be so designed to contain cysteine residues at two or more fixed positions and thus code for cyclic peptides. As discussed further below, a preferred bacteriophage fd (e.g., from libraries L3.6, L3.15, L8.15) is a filamentous phage having dimensions of approximately 7 nm by 500–900 nm . On its surface, the phage expresses primarily two different proteins, the gene III protein, of which there are 3–5 copies per phage particle, and the gene VIII protein, of which there are approximately 2,500 copies. In the phage display system, the genes coding for either gene III or gene VIII have been modified to code for and express random peptide sequences of a particular length, such as 6-mer, 15-mer and 30-mer. In addition, multiple copies of a DNA insert coding, for example, for a random 15-mer sequence can facilitate the production of random peptide sequences longer than 15-mer. Each library represents between $10^8$ and $10^9$ or more random peptide sequences. As such, the phage library can simulate a nanoparticle mixture in which the nanoparticles are coated with different peptides of a specified length.

During the construction of phage display libraries it is possible that more than one DNA insert (or partial DNA inserts which may arise due to clevage at internal restriction sites in the DNA library or DNA insert) can be cloned into the cloning sites in gene III or gene VIII, resulting in multiple DNA inserts in the resulting vector clone. Such clones containing multiple DNA inserts, or derivatives thereof, have the capacity to code for longer than expected peptides, due to the presence of the multiple DNA inserts, provided the DNA inserts are in-frame with respect to the gene III or gene VIII reading frame and/or provided the clones contain internal DNA sequences which are prone to or suseptible to the process of ribosomal frameshifting during translation in vivo, which in turn can restore the reading frame of the DNA insert with respect to the translational reading frame of gene III or gene VIII, and/or provided the mRNA coded by the DNA insert is in-frame with gene III or gene VIII and does not contain internal translational stop or translational termination codons, and/or provided any internal translational stop or termination codon (s) can be read as a reading codon(s) by a translational suppressor molecule in vivo, such as the TAG codon which is decoded by the SupE suppressor in *E. coli* as a GLN codon.

The peptides coded by triple (or multiple) DNA inserts have the capacity to code for longer and/or more diverse peptides. Such longer peptides have a greater capacity to adopt secondary and tertiary structures as opposed to shorter peptides, such as a 15-mer peptide. This capacity of peptides to adopt defined secondary and/or tertiary structures coded by those phages containing multiple or triple DNA inserts may in-turn account for the selection of these types of phages from random phage display libraries during selection or panning procedures.

Different transport mechanisms operate in epithelial cells. Some transport mechanisms are carrier mediated, whereby a carrier or receptor will bind to a ligand and transport the bound ligand into or through the epithelial cell. Other transport systems operate by transcytosis, whereby a carrier or receptor site will bind a ligand, the carrier: ligand complex is internalized by endocytosis and thus delivers a ligand (or drug) into or through the cell. This invention allows for the discovery of certain peptide sequences that bind to such active carrier or transcytotic transport systems to facilitate drug delivery. However, rather than focusing on one receptor/carrier system, the invention discloses the use of a blind or random or preselected screening approach in order to identify peptide sequences that interact with undefined or unknown receptor/carrier sites in tissues, such as epithelial cells, and facilitates the delivery of bacteriophage from the apical to basolateral side of polarized cell cultures or model tissue systems. Because these peptide sequences can facilitate the delivery of a bacteriophage, they are likely to be useful in the transport of drugs and particulate systems, especially the transport of drug loaded or encapsulated nano- and microparticulate systems when coated onto the surface of the same or fusion proteins whereby the peptide is fused to a therapeutic peptide or protein. In addition, this invention allows for the discovery of certain peptide sequences that recognize transcellular or paracellular transport routes or mechnisms in cultured cells or tissues and so facilitate drug delivery by these transport pathways.

In brief, the screening approach in the in vitro context includes contacting a predetermined amount of phage from a random phage library or a preselected phage library with a first side of a human or animal tissue sample or polarized tissue cell culture, harvesting phage which is transported to the opposite side of the tissue sample or culture to select transported phage, amplifying the transported phage in a host and identifying at least one random peptide coded by a transported phage to identify a peptide which permits or facilitates the transport of an active agent through a human or animal tissue. If desired, the contacting, harvesting and amplifying steps can be repeated a predetermined number of times using the transported phage obtained in the previous cycle. For instance, using polarized tissue cell culture samples such as Caco-2 cells or T-84 cells or tissue extracts such as isolated rat colon segments, phage can be plated to the apical side of the cultured cells or tissue segments. Subsequently, at any desired timepoint but usually from 1 hour to 24 hours, the basolateral medium is harvested aseptically and used to reinfect a host, such as male $E.$ $coli$ coding for the $F^1$ Factor, to produce progeny. The selected phage from cycle one can be applied to the apical side of the cultured cells or tissue segment and again the phage in the basolateral medium is collected, titered and amplified. Repetition of this cycle allows for enrichment of phage capable of being transported from the apical to basolateral side and thus, the % yield of phage appearing in the basolateral medium increases as the number of cycles increase. After repeating this cycle from 0 to 30 times, preferably 3 to 20 times, the DNA sequence coding for the $NH_2$-terminal region of the pIII or pVIII protein of the purified, selected, amplified phage(s) is determined to permit deduction of the amino acid sequence of the modified phage(s) which confers the advantage of transport from the apical to basolateral side of the cultured or tissue system.

Similar to the in vitro screening approach given above, the screening approach in the in vivo context includes contacting a predetermined amount of phage from a random phage library or a preselected phage library with a first side of a tissue barrier in vivo, harvesting phage which is transported to the opposite side of the tissue barrier to select transported phage, amplifying the transported phage in a host and identifying at least one random peptide coded by a transported phage to identify a peptide which permits or facilitates the transport of an active agent through a human or animal tissue. If desired, the contacting, harvesting and amplifying steps can be repeated a predetermined number of times using the transported phage obtained in the previous cycle. For instance, the phage display library can be purified such as by either polyethylene glycol precipitations or sucrose density or CsCl density centrifugations. The purified library can then be resuspended, such as in TBS or PBS buffer, and introduced onto one side of a tissue barrier, such as injected into the duodenum, jejunum, ileum, colon or other in vivo animal site using, for instance, a closed loop model or open loop model. Following injection, samples of bodily fluids located across the tissue barrier, such as samples of the portal circulation and/or systemic circulation, are withdrawn at predetermined time points, such as 0 to 90 minutes and/or 2 to 6 hours or more. An aliquot of the withdrawn sample (e.g., blood) is used to directly infect a host, such as $E.$ $coli,$ in order to confirm the presence of phage. The remaining sample is incubated, such as overnight incubation with $E.$ $coli$ at 37° C. with shaking. The amplified phage present in the culture can be sequenced individually to determine the identity of peptides coded by the phage or, if further enrichment is desired, can be PEG precipitated, resuspended in PBS, and can be either further PEG-precipitated or used directly for administration to another animal closed or open GIT loop model system followed by collection of portal or systemic blood sample and subsequent amplification of the phage transported into such circulation systems. In this manner, administration of the phage display library with, if desired, repeat administration of the amplified phage to the GIT of the animal permits the selection of phage which are transported from the GIT to the portal and/or systemic circulation of the animal.

If desired, following administration of the phage display library to the tissue barrier (e.g., GIT) of the animal model, the corresponding region of the tissue barrier can be recovered at the end of the procedures given above. This recovered tissue can be washed repeatedly in suitable buffers, such as PBS containing protease inhibitors and homogenized, such as in PBS containing protease inhibitors. The homogenate can be used to infect a host, such as $E.$ $coli,$ thus permitting amplification of phages which bind tightly to the tissue barrier (e.g., intestinal tissue). Alternatively, the recovered tissue can be homogenized in suitable PBS buffers, washed repeatedly and the phage present in the final tissue homogenate can be amplified in $E.$ $coli.$ This approach permits amplification (and subsequent identification of the associated peptides) of phages which either bind tightly to the tissue barrier (e.g., intestinal tissue) or which are internalized by the cells of the tissue barrier (e.g., epithelial cells of the intestinal tissue). This selection approach of phage which bind to tissues or which are internalized by tissues can be repeated.

Subsequently, the corresponding peptide sequences coded by the selected phages, obtained by the procedures above and identified following DNA sequencing of the appropriate gene III or gene VIII genes of the phage, are synthesized. The binding and transport of the synthetic peptide itself across the model cell culture or isolated tissue system (such as colonic) permits direct assessment of the transport characteristics of each individual peptide. In addition, fusion of the selected peptide(s) sequences with other peptides or proteins permits direct assessment of the transport of such chimeric proteins or peptides across the model systems. Such chimeric proteins or peptides can be synthesized either in vitro or by conventional recombinant technology techniques whereby the cDNA coding for the transporting peptide and the cDNA coding for the drug peptide or protein are ligated together in-frame and are cloned into an expression vector which in turn will permit expression in the desired host, be it prokaryotic cells or eukaryotic cells or transgenic animals or transgenic plants. For instance, the cDNAs coding for the modified $NH_2$-terminal region of the pIII proteins can be subcloned into the genes or cDNAs coding for selected protein molecules (e.g., calcitonin, insulin, interferons, interleukines, cytokines, EPO, colony stimulating factors etc.) and these modified genes or cDNAs can be expressed in E. coli or suitable mammalian cells or transgenic animals or transgenic plants. The expressed recombinant proteins can be purified and their transcellular, carrier-mediated, transcytotic and/or paracellular transport across human or animal tissue can be verified. In addition, the transporting peptides can be used to coat the surface of nanoparticulate or microparticulate drug delivery vehicles. Such coatings can be performed by either direct adsorption of the peptide to the surface of the particulate system or alternatively by covalent coupling of the peptide to the surface of the particulate system, either directly or via a linking moiety or by covalent coupling of the peptide to the polymers used in the production of nanoparticulate or microparticulate drug delivery vehicles, followed by the utilization of such peptide:polymer conjugates in the production of nanoparticulate or microparticulate drug delivery vehicles.

Description and Preparation of Phage Display Libraries

Three phage display libraries, identified herein as L3.6, L3.15 and L8.15, were obtained from Prof. George P. Smith at the University of Missouri-Columbia. Each library is in the vector fUSE5, which was derived from the parent vector "fd-tet". In the library L3.6, random 6-mer libraries are expressed by the gene III of the fd bacteriophage and are displayed on all 5 copies of the resulting protein pIII proteins. The number of transductant clones amplified is $3.7 \times 10^{11}$ and the size of phage DNA is 9225 bases. In the library L3.15, random 15-mer libraries are expressed by the gene III of the fd bacteriophage and are displayed on all 5 copies of the resulting protein pIII proteins. The number of transductant clones amplified (primary amplification) is $3.2 \times 10^{11}$; (secondary amplification) is $12.1 \times 10^{12}$ and the size of phage DNA is 9252 bases. In the library L8.15, the vector has two genes VIII in the same genome, one of which is wild type and the other of which displays the foreign residues. The random 15-mer libraries are expressed by one of the two genes VIII of the fd bacteriophage and are displayed on up to approximately 300 copies of the resulting recombinant protein pVIII proteins. This vector is called f88-4, in which the foreign 15-mer is displayed on up to approximately 300 copies of protein pVIII. The number of transductant clones amplified is $2.2 \times 10^{12}$ and the size of phage DNA is 9273 bases.

A 30-mer phage display library, X30, was obtained from Dr. Jamie S. Scott of Simon Fraser University. The X30 phage display library codes for random peptide sequences 30 residues in size. This library was constructed in the f88.4 vector, which carries a tetracycline resistance gene and has two pVIII genes: the wild type gene and a synthetic gene. The f88.4 library has variable inserts cloned into the synthetic pVIII gene of the f88.4 vector.

D38 and DC43 are random phage display libraries in which gene III codes for random peptides of 38 and 43 residues in size, respectively.

A large scale preparation of each of the bacteriophage libraries was made in the E. coli host strain K91 Kan. A single K91Kan colony was innoculated into a sterile 50 ml tube containing 20 ml LB broth (Yeast extract (Gibco)—1 g; Tryptone (Gibco)—2 g; NaCl—1 g; and distilled water—200 ml) together with kanomycin (final concentration 100 µg/ml) and grown to mid log phase with 200 rpm agitation at 37° C. (OD 0.45 at 600 nm). The cells were allowed to incubate with gentle shaking (100 rpm, 37° C.) for 5 min to regenerate sheared F pili. The cells were pelleted by centrifugation at 2200 rpm for 10 min at room temperature, the supernatant removed and the cells gently resuspended in 20 ml 80 mM NaCl and shaken gently (100 rpm, 37° C.) for 45 min. The cells were centrifuged again and the cell pellet was gently resuspended in 1 ml cold NAP buffer (NaCl (5 M stock)—1.6 ml; $NH_4H_2PO_4$ (0.5 M stock, pH 7.0)—10 ml; and distilled water—88.4 ml). The cells were stored at 4° C. and remained infectable for 3–5 days.

The primary libraries were amplified by inoculating two 1 l flasks containing 100 ml terrific broth with 1 ml of an overnight culture of K91Kan cells (grown in LB +100 µg/ml kanamycin). This culture was incubated at 37° C. and 200 rpm until the $OD_{600}$ of a 1:10 dilution was 0.2 and then further incubated for 5 min at 37° C. and 200 rpm to allow sheared F pili to regenerate. 10 µl of the primary library was added to each flask with continued slow shaking for 15 min. Each culture was poured into a prewarmed 2 l flask containing 1 l LB +0.22 µg/ml tetracycline and shaken at 200 rpm for 35 min. 1 ml of 20 mg/ml tetracycline was added and 7 µl samples were removed from each flask. The flasks were replaced in an incubator with continued shaking overnight. 200 µl of various serial dilutions ($10^{-4}$, $10^{-6}$, $10^{-8}$, $10^{-10}$ dilutions) of each culture were spread on LB+40 µg/ml tetracycline and 100 µg/ml kanamycin plates and incubated overnight. The colonies were counted.

Large scale purification of phage was accomplished by dividing the culture evenly between two 500 ml centrifuge tubes and centrifuging at 5,000 rpm for 10 min at 4° C. The supernatants were transferred to fresh tubes and recentrifuged at 8,000 rpm for 10 min at 4° C. The final cleared supernatants were poured into fresh tubes and the net volume was noted. 0.15 vol PEG/NaCl (PEG 8000—100 g; NaCl—116.9 g; and distilled water—475 ml) was added and the tubes were mixed gently by inversion (×100 times) and stored on ice for>4 h (or overnight at 4° C.). Following centrifugation at 8,000 rpm for 40 min at 4° C., the supernatant was decanted, recentrifuged briefly and residual supernatant was removed by pipetting. 10 ml TBS (Tris HCl (pH 7.5)—0.60 g; NaCl—0.88 g; and distilled water—100 ml) was added and the tube was incubated at 37° C. and 200 rpm for 30 min to dissolve pellet. The tube was centrifuged briefly and the solutions from both tubes were transferred to a single Oak Ridge tube, centrifuged at 10–15,000 rpm for 10 min at 4° C. and the supernatant was removed to a fresh tube. 0.15 vol PEG/NaCl was added and the phage were allowed to precipitate on ice for 1 h. The procedures from the addition of 10 ml TBS were repeated. Into a tared 30 ml Beckman polyallomer tube, 4.83 g CsCl was added, the tube retared and the phage solution was added. TBS was added to a net weight of 10.75 g (total volume 12 ml of a 31% w/w solution of CsCl, density 1.3 g/ml). A ratio of 31:69 w/w ratio is essential. Following centrifugation in the ultracentrifuge at 20,000 rpm and 4° C. for 48 h, the tube was illuminated from the top with a visible light source and identify the phage band:

Phage band—upper band, approximately 5 mm, faint, blue, non-flocculent

PEG—lower band, narrow, stringy, flocculent, opaque, white

The fluid was aspirated off to 2 mm above the phage band and the phage band was withdrawn using a sterile wide aperture transfer pipette and placed in a 26 ml polycarbonate centrifuge tube. The tube was filled to the shoulder with TBS, mixed and centrifuged at 50,000 rpm for 4 h at 4° C. in the 60Ti rotor (repeated). The pellet was dissolved in 10 ml TBS by gentle vortexing and allowed to soften overnight in the cold and revortexed (repeated). The pellet was then dissolved in TBS (2 ml per liter of original culture) by vortexing, allowed to soften overnight at 46° C. and revortexed. The tube was centrifuged briefly to drive solution to the bottom of the tube and transferred to 1.5 ml microtubes. Sodium azide (0.02%) can be added and the solution can be heated to 70° C. for 20 min to kill residual microorganisms. Following microfuging for 1 min to clear the solution, the supernatant was transferred to sterile microtubes and stored at 4° C. 200 $\mu$l of a 1:100 dilution was scanned from 240–320 nm to determine the concentration of physical particles and titre 10 $\mu$l of a $10^{-8}$ dilution on 10 $\mu$l of starved K91Kan cells. 200 $\mu$l of the infections was spread on LB (+40 $\mu$g/ml tetracycline and 100 $\mu$g/ml kanamycin) plates, incubated at 37° C. for 24 h and counted the number of colonies to determine the titre of infectious units in the phage stocks.

Culturing of Caco-2, T-84 cells

The Caco-2 (ATCC designation: CCL 248; derived from a lung metastasis of a colon carcinoma in a 72-year old male) and T-84 cells (ATCC designation: HTB 37; isolated from a primary colonic tumor in a 72 year old Caucasian male) were cultured initially in 25 $cm^2$ flasks, until they reached confluency. T84 cells were grown in 1:1 DMEM-:Ham's F12 medium containing 2 mM glutamine, 15 mM BEPES, 10% fetal calf serum (FCS), 1% MEM non essential amino acids and 50U $ml^{-1}$ penicillin and 50 $\mu$g $ml^{-1}$ streptomycin. Caco-2 cells were grown in DMEM+glutamax-1 containing 10% FCS, 1% MEM non essential amino acids, 50U $ml^{-1}$ penicillin and 50 $\mu$g $ml^{-1}$ streptomycin. All cells were incubated at 37° C. in 95% $O_2$/5% $CO_2$. At confluence the cells were used to seed snapwells.

The seeding of snapwells was essentially as follows for T-84 cells (a concentration of $1 \times 10^6$ cells/1.0 ml of medium is required for each 12 mm snapwell; a 100% confluent flask of T84 contains approximately $8 \times 10^6$ cells and would be sufficient to seed 8 snapwells). The flasks were trypsinised and cells were carefully resuspended, making sure there are no clumps or air bubbles. 2.6 ml of tissue culture medium is placed in the bottom of the wells and 0.1 ml on the filter and placed in the incubator for 10 mins at 37° C. 1.5 ml of the cell suspension was added to each filter, being careful not to let any fall into the bottom of the well. The filter was placed back in the incubator and checked after 24 hrs. The cells were routinely monitored for adequate TER using an EVOM chopstick epithelial voltometer (WPI). In the case of Caco-2 cells, the seeding of Caco-2 cells was essentially the same as for T-84 cells except that they are seeded at $5 \times 10^5$ rather than $1 \times 10^6$ cells/ snapwell.

The subsequent maintenance and feeding of the cells on the snapwells was as follows: when feeding the wells, the medium was removed from the basolateral side of the snapwell first. The medium was removed from the monolayer with a pipette being careful not to touch the filter and then 1 ml of growth medium was place onto the apical side and 2 ml of growth medium into the basolateral side. Spillages of medium on the sides of the plate outside the well were checked for and swabbed with a cotton bud moistened with alcohol if necessary. Following seeding on the snap wells, the cells were fed on a daily basis and were cultured on the snapwells for between 21–30 days, during which time the cells spontaneously differentiated and become polarized.

Preparation of Intact Rat Colon Mucosae Tissue

Animals are sacrificed (by carbon monoxide), the abdominal cavity was opened and the colon was located, removed and washed in 1×Hank's Balanced Salt Buffer (HBSS; Gibco BRL, Cat #14065–031). The tubular segment was cut along the mesenteric border to give a flat square piece of tissue. The smooth muscle layer was then removed by blunt dissection to leave an approximate 2.5 $cm^2$ patch of epithelium.

The isolated rat colonic mucosae were mounted in Side-by-side Sweetana-Grass (SG) diffusion chambers. The mounted rat colonic mucosae in the S-G chambers were used in the analysis. of phage transport from the apical to basolateral side of the colonic tissue.

Balancing Side-by-side Chambers

The water bath was allowed to equilibrate to 37° C. The chambers were filled with HBSS Buffer (see below) and the electrodes are switched on. The input-offset control knob was adjusted to zero. The system was allowed to equilibrate for approximately 20 minutes, making sure the readings remain at zero throughout. The electrodes were switched off and HBSS solution removed. Filters containing sheets of the rat colonic epithelium were mounted on the apparatus and 10 mls of HBS S Buffer was added to each side simultaneously. The tissues were oxygenated with 95% $O_2$/5% $CO_2$ and the system was allowed to equilibrate for at least 30 minutes. Electrodes were switched on and the knobs set to voltage clamp and current. Voltage was adjusted to give a change in current of approximately 2–3 $\mu$A. The timer was then set to apply a voltage every 8 mins and the corresponding deflected current was used to calculate TER by applying the following Ohmic relationship: R=V/I. Recordings were commenced for at least 10 min before any phage was added.

Enzyme Linked Immuno-sorbent Assay (ELISA) for fd-derived Phage on Caco-2 Cells

Caco-2 cells (100 $\mu$l) were grown to confluence in 96 well tissue culture plates ($2 \times 10^5$ cells/well grown for 2 days in growth medium containing DMEM/Glutamax +1% Pen/Strep, 1% MEM & 10% FCS). After two days growth, 100 $\mu$l of 10% formaldehyde [Formaldehyde (38%) sterile distilled water (1:3 vol)] was added to the confluent Caco-2 cell monolayers followed by incubation for 15 min at room temperature. The contents of the microtitre wells was emptied by inversion/flicking and the wells were washed three times with DPBS (Dulbecco's PBS). Each well was filled with 200 $\mu$l of 0.1% phenylhydrazine-DPBS (0.1% phenylhydrazine in DPBS) and incubated for 1 h at 37° C. Subsequently, the contents of the microtitre wells were emptied by inversion/flicking and the wells were washed three times with DPBS. 200 $\mu$l of 0.5% BSA in DPBS was added to each well followed by incubation for 1 h at room temperature. Each well was next washed three times in 1% BPT (1% BSA, 0.05% Tween 20 in DPBS).

Phage samples (100 $\mu$l in 1% BPT) (either neat phage at $10^{10}$ pfu/ml or 1:25 or 1:100 dilutions thereof) were added to the wells, followed by incubation at room temperature for 2 h. The contents of the microtitre wells were removed by inversion/flicking and the wells were washed five times in 1% BPT. 100 $\mu$l of horse radish peroxidase (HRP) -anti-M13 conjugate (HRP/anti-M13 conjugate:horseradish peroxidase conjugated to sheep anti-M13 IgG, 1:5000 working dilution in 1% BPT; Pharmacia 27-9402-01) was added to to each well, followed by incubation for 1 h at room temperature. The contents of the microtitre wells were again removed by inversion/flicking and the wells were washed five times in 1% BPT. 200 µl of TMB substrate solution (3,3', 5',5-tetramethylbenzidine; Microwell Peroxidase Substrate System; Kirkegaard & Perry Laboratories CN 50-76-00; prepared by mixing equal amounts of TMB Peroxidase Substrate A and Peroxidase Solution B in a glass container immediately before use) was added to each well, followed by incubation at room temperature for 20–60 min. Thereafter, absorbance readings were read at 650 nm on a microtitre plate reader.

Processing of Intestinal Tissue

For use in the in vivo embodiment described herein, the phage display library is purified such as by either PEG precipitation or by sucrose or CsCl density centrifugation. The phage display library is resuspended in PBS (or TBS) buffer and injected into the in vivo animal site, such as duodenum, jejunum, ileum, colon, ascending colon, transverse colon, descending colon, pelvic colon in the closed (or open) animal (rat, rabbit or other species) loop model. Following administration of the phage display library to the gastro-intestinal tract of the animal model, and withdrawal of portal and/or systemic blood samples at predetermined time points (such as 0 min, 15 min, 30 min, 45 min, 60 min up to 6 hours), or incubation of the administered phage display library in the closed (or open) loop model for a predetermined period of time, the corresponding region of the GIT track exposed to or incubated with the phage display library can be recovered at the end of the experiments. Following repeated washings of the recovered intestinal tissue in suitable buffers such as PBS containing protease inhibitors, the washed tissue is homogenised in PBS containing protease inhibitors and the homogenate is used to infect *E.coli*, thus permitting amplification of phages which can bind tightly to the intestinal tissue. Alternatively, the recovered intestinal tissue can be homogenised in suitable PBS buffers, washed repeatedly and the phage present in the final tissue homogenate can be amplified in *E. coli*. This latter approach also permits amplification of phages which either bind tightly to the intestinal tissue or which are internalized by the epithelial cells of the intestinal tissue

Selection of Phage with Enhanced Ability to Cross Cellular Barriers

A. Treatment of Tissue Culture Cell Monolayers (Snapwell Models) with Phage display Populations In a laminar flow cabinet, 100 µl of phage solution was mixed with 900 µl of growth medium without antibiotic (the complete recommended medium for each cell line but with no antibiotics added) in a microfuge tube. The experiment was carried out in duplicate and included a control treatment containing no phage. The TER was measured for each snapwell, noting the age of the cells and the passage number. Only intact monolayers of recommended age were used which had expected TER. The basolateral medium was replaced in the snapwells with medium without antibiotic and the apical medium was removed. The phage solutions and control solutions were added to the apical side of the cells and the snapwell cultures were incubated as normal. At each harvest time point (e.g., 1 h, 5 h, 24 h after application of phage), the medium was removed from the basolateral side and stored in a sterile 2 ml screwcap tube at 4° C. At each time that the basolateral medium is removed, the medium was replaced with fresh medium without antibiotic. When the experiments are finished, the TER was measured and the monolayers were treated with Vircon disinfectant as per normal.

The phage were titrated by preparing starved cells of *E. coli* K91Kan and carrying out serial dilutions of phage in the (growth medium above) in TBS/gelatin. 10 µl of starved cells and 10 µl of serially-diluted phage solution were mixed in a 1.5 ml microfuge tube. The phage was allowed to infect for 10 min at room temperature. In general, the following dilutions are used:

| Sample | Dilution |
| --- | --- |
| t = 1 h | neat or $10^{-1}$ |
| t = 5 h | $10^{-1}$, $10^{-3}$ |
| t = 24 h | $10^{-1}$, $10^{-3}$ |
| Apical/amplified | $10^{-6}$, $10^{-7}$, $10^{-8}$ |

1 ml of LB medium containing 0.2 µg ml$^{-1}$ tetracycline was added to the phage/K91kan cell mixtures and incubated for 30 min at 37° C. 200 µl of the phage/K91Kan cell mixture was spread on LB agar plates containing 40 µg ml$^{-1}$ tetracycline and 100µg/ml kanomycin and grown overnight at 37° C. For a $10^{-2}$ dilution (10 µl into 990 µl), 200 colonies on a plate represents 1×10$^7$ TU ml$^{-1}$.

Thus, by estimating the titre of phage which was present in the basolateral medium and by knowing the number of phage that was applied to the apical side, an estimate of the % yield of phage transported to the basolateral medium from the apical side can be made.

Selected phage present in the basolateral growth medium were amplified by adding 150 µl of PEG/NaCl per 1 ml of phage solution (pool the harvest from all the three time-points (eg. 3×2 ml=6 ml) in an Oak Ridge tube. The solution is mixed very well by continuously inverting for 2–3 min and stored at 4° C. for at least 4 h. The precipitated phage is centrifuged for 15 min at 10,000 g (8,500 rpm using Beckman JA17 rotor) in a Beckman J2-MC preparative ultracentrifuge. The supernatant was removed and recentrifuged as before for 5 min. The pellet was resuspended in 100 µl of TBS by leaving for 5 min at room temperature and vortexing (repeat by leaving for 15 min and vortexing again). The suspended phage solution was placed in an Oak Ridge tube and 100 µl of starved *E.coli* K91Kan cells were added. The phage/cell solution was mixed gently and left at room temperature for 30 min. 20 ml of prewarmed LB medium containing tetracycline (0.2 µg ml$^{-1}$) and kanomycin (100 µg/ml) was added and incubated at 200 rpm at 37° C. for 30 min. 10 µl of stock tetracycline (40 mg ml$^{-1}$) was added to the medium and the tube was incubated overnight. The overnight culture was centrifuged for 15 min at 3440 g (5,000 rpm using Beckman JA17 rotor) in a Beckman J2-MC preparative ultracentrifuge. The supernatant was added to a clean (preferably sterile) Oak Ridge tube and centrifuged again for 10 min at 13800 g (10,000 rpm). The supernatant was placed in a clean (preferably sterile) Oak Ridge tube containing 3 ml of PEG/NaCl and mixed by continuous inversion for 2–3 min. Following storage at 4° C. for at least 4 h, the tube was centrifuged for 15 min at 13800 g (10,000 rpm using Beckman JA17 rotor) in a Beckman J2-MC preparative ultracentrifuge. The supernatant was removed and recentrifuged as above for 5 min at 10,000 rpm. As much supernatant as possible was removed with a micropipette and the pellet was resuspended in 1 ml of TBS by leaving for 5 min at room temperature and vortexing. The resuspension was left for 15 min and vortexed again. The phage solution was transferred to a 1.5 ml microfuge tube and vortexed again. The solution was centrifuged at 13,000 rpm for 30 s in a microfuge and the supernatant was transferred to a fresh 1.5 ml microfuge tube containing 150 $\mu$l PEG/NaCl. The tube was mixed by inverting for 2–3 min and stored at 4° C. for at least 1 h. Subsequently, the tube was centrifuged at 13,000 rpm for 10 min in a microfuge and the supernatant was removed and recentrifuged for 5 min. The pellet was resuspended in 100 $\mu$l of TBS by leaving for 5 min at room temperature and vortexing. The resuspension was left for 15 min and vortexed again. This resuspension represents the phage selected in cycle 1. One $\mu$l should be withdrawn and used for titration to confirm that approximately $10^9$ TU are present.

The phage solution is now ready for a further round of selection in the cultured T84 and Caco-2 cells, by repeating the steps above using the phage transported into the basolateral medium. Thus, phage selected from cycle one is now reapplied to the apical side of the Caco-2 or T-84 cells growing on Snapwells. In general, in each cycle the same titre of phage is applied to the apical side of the cells growing on snapwells. At the end of each cycle the titre of phage present in the basolateral medium at each time point is determined and these transported phage are reamplified and recycled back through the cells. Thus, the % yield of phage which appear in the basolateral medium increases as the number of cycles increase. At the end of cycle five, phage have been selected which are preferentially transported from the apical to basolateral side of the cultured cells, due to the random peptide sequences displayed by the bacteriophage gene III or gene VIII protein products.

B. Treatment of Intact Rat Colon Mucosae Tissue with Phage Display Populations

Once the rat colonic tissue is set up as described above, approximately $1\times10^{11}$ phage in HBSS buffer were applied to the gut side of the colonic tissue, after the electrodes were switched off. Subsequently, at indicated time points, the settings were changed to voltage and amplify, the system was grounded, the medium on both the gut side and blood side of the colonic tissue were simultaneously removed, and the medium on the blood side was saved at 4° C. The original medium present on the gut side was replaced onto the gut side of the mounted colonic tissue in the S-G chambers. Simultaneously fresh HBSS buffer medium was added to the blood side, and the tissues were oxygenated with 95% $O_2$/5% $CO_2$. Electrodes were switched on again and the knobs set to voltage clamp and current. Voltage was adjusted to give a change in current of approximately 2–3 $\mu$A. The timer was then set to apply a voltage every 8 mins and the corresponding deflected current was used to calculate TER by applying the following Ohmic relationship: $R=V/I$.

The phage post transfer across rat colon was titrat and amplified as follows (phage samples titred prior to and after amplification). Serial dilutions of phage (2 $\mu$l phage+18 $\mu$l TBS/gelatin) were performed in microtitre plates and 10 $\mu$l volumes of the required dilutions were transferred to 1.5 ml microtubes. 10 $\mu$l of starved K91Kan cells were added to each microtube, mixed gently and incubated at room temperature for 10 min. 990 $\mu$l of LB+0.2 $\mu$g ml$^{-1}$ tetracycline were added and the microtubes were incubated at 37° C. for 30 min. 200 $\mu$l of the culture were spread on LB (40 $\mu$g ml$^{-1}$ tetracycline +100 $\mu$g ml$^{-1}$ kanamycin) agar plates, incubated at 37° C. overnight and the number of colonies were counted.

The phage was amplified by adding 150 $\mu$l of PEG/NaCl to 1 ml of phage solution (i.e., apical or basolateral BSS buffer from chambers) in an Oak Ridge tube, mixing by inversion ($\times$100) and incubating at 4° C. for 4 h. The tube was centrifuged at 10,000 g for 15 min (JA17 rotor; 8,500 rpm) and the supernatant was decanted and recentrifuged for 5 min. The supernatant was removed and the pellet was resuspended in 100 $\mu$l of TBS (leave at room temperature for 5 min, vortex, leave at room temperature for 15 min and revortex). A 5 $\mu$l sample was retained for titration. 100 $\mu$l of starved K91Kan cells were added to 95 $\mu$l of phage solution, mixed gently and incubated at room temperature for 30 min. 20 ml of pre-warmed LB +0.2 $\mu$g ml$^{-1}$ tetracycline were added and the tube was incubated at 37° C. and 200 rpm for 30 min. 10 $\mu$l of tetracycline (40 mg ml$^{-1}$ stock) and kanomycin (final concentration of 100 $\mu$g/ml) were added and the tube was incubated overnight at 37° C. and 200 rpm. The tube was then centrifuged for 15 min at 3440 g (JA17 rotor; 5,000 rpm), the supernatant was added to a new Oak Ridge tube and recentrifuged at 13,800 g (JA17 rotor; 10,000 rpm). The supernatant was transferred to a new Oak Ridge tube containing 3 ml of PEG/NaCl, mixed by inversion ($\times$100) and incubated at 4° C. for 4 h. The tube was then centrifuged at 13,800 g, the supernatant decanted and recentrifuged at 13,800 g for 5 min. The pellet was resuspended in 100 $\mu$l of TBS (leave at room temperature for 5 min, vortex, leave at room temperature for 15 min and revortex). The phage solution was transferred to a microtube containing 150 $\mu$l of PEG/NaCl, mixed by inversion ($\times$100) and incubated at 4° C. for 1 h. The tube was microfuged for 1 min, the supernatant removed and remicrofuged. The supernatant was removed and the pellet resuspended in 100 $\mu$l of TBS (leave at room temperature for 5 min, vortex, leave at room temperature for 15 min and revortex). 2 $\mu$l of phage for was removed for titration while the rest was stored at 4° C.

The phage solution is now ready for a further round of selection in the S-G mounted rat colonic tissue, by repeating the steps above using the phage transported into the basolateral medium. Thus, phage selected from cycle one is now reapplied to the apical or gut side of the S-G mounted rat colonic tissue. In general, in each cycle the same titre of phage is applied to the gut side of the tissue. At the end of each cycle the titre of phage present in the basolateral medium (blood side) at each time point is determined and these transported phage are reamplified and recycled back through the colonic tissue. Thus, the % yield of phage which appear in the basolateral medium increases as the number of cycles increase. At the end of cycle five or six we have selected for phage which are preferentially transported from the apical or gut side of the colonic tissue to blood side or basolateral side of the colon tissue, due to the random peptide sequences displayed by the bacteriophage gene III or gene VIII protein products.

C. Treatment of Animal Tissue Barriers In Vivo with Phage Display Populations

The purified phage display library (random or preselected) is diluted to 500 $\mu$l in PBS buffer and injected into the closed (or open) intestinal loop model (e.g., rat, rabbit or other species). At time 0 and at successive time points after injection, a sample of either the portal circulation or systemic circulation is withdrawn. An aliquot of the withdrawn blood can be incubated with E. coli, followed by plating for phage plaques or for transduction units or for colonies where the phage codes for resistance to antibiotics such as tetracycline. The remainder of the withdrawn blood sample (up to 150 $\mu$l) is incubated with 250 $\mu$l of E. coli and 5 ml of LB medium or other suitable growth medium. The

*E. coli* cultures are incubated overnight by incubation at 37° C. on a shaking platform. Blood samples taken at other time points (such as 15 min, 30 min, 45 min, 60 min up to 6 hours) are processed in a similar manner, permitting amplification of phages present in the portal or systemic circulation in *E. coli*. at these times. Following amplification, the amplified phage is recovered by PEG precipitation and resuspended in PBS buffer or TBS buffer. In addition, the titer of the amplified phage, before and after PEG precipitation is determined. The amplified, PEG precipitated phage is diluted to a known phage titer (generally between $10^8$ and $10^{10}$ phage or plaque forming units per ml) and is injected into the GIT of the animal closed (or open) loop model. Blood samples are collected from portal and/or systemic ciruclation at various time points and the phage transported into the blood samples are amplified in *E. coli* as given above for the first cycle. Subsequently, the phage are PEG precipitated, resuspended, titered, diluted and injected into the GIT of the animal closed (or open) loop model. This procedure of phage injection followed by collection of portal and/or systemic blood samples and amplification of phage transported into these blood samples can be repeated, for example, up to 10 times, to permit the selection of phages which are preferentially transported from the GIT into the portal and/or systemic circulation.

EXAMPLE 1

% Yield of φ in Caco-2 Cells

Libraries L3.6, L3.15, L8.15 and fUSE2 (control) were screened using Caco-2 cells according to the procedures given above. The percentage yields per cycle (1 hr, 5 hr, 24 hr and total yield) and the change in transepithelial resistance for the cycles were measured. The TER measurements for the Caco-2 cells remained in the range 224–449 $\Omega$ cm$^{-2}$. The phage yield on the basolateral side of the cell culture is reported as a percentage of the phage applied to the apical side. Six successive screening cycles were performed and 1 hr, 5 hr and 24 hr samples of the basolateral buffer were harvested. The percentage yields of phage obtained per cycle in cycles 1–6 are summarized in Table 1. Usable yields were generally obtained by the 4th cycle.

EXAMPLE 2

% Yield of φ in T-84 Cells

Libraries L3.6, L3.15, L8.15 and fUSE2 (control) were screened using T-84 cells according to the procedures given above. The percentage yields per cycle (1 hr, 5 hr, 24 hr and total yield) and the change in transepithelial resistance for the cycles were measured. The TER measurements for the T-84 cells remained in the range 224–449 φ cm$^{-2}$. The phage yield on the basolateral side of the cell culture is reported as a percentage of the phage applied to the apical side. Four successive screening cycles were performed and 1 hr, 5hr and 24 hr samples of the basolateral buffer were harvested. The percentage yields of phage obtained per cycle in cycles 1–4 are summarized in Table 2. Usable yields were generally obtained by the 4th cycle.

EXAMPLE 3

% Yield of φ in Isolated Colon Segments

A phage mixture comprising libraries L3.6, L3.15 and L8.15 was screened using isolated rat colon according to the procedures given above. The phage yield on the basolateral side of the tissue sample is reported as a percentage of the phage applied to the apical side. Six successive screening cycles were performed and four 1 h samples of the basolateral buffer were harvested. Table 3 reports the % yield of φ in isolated colon segments.

TABLE 1

% YIELD OF φ IN CACO-2 CELLS

| | Time (hours) | | | |
|---|---|---|---|---|
| Round | 1 | 5 | 24 | Total |
| Library L3.6 | | | | |
| 1 | $9 \times 10^{-4}$ | $9 \times 10^{-4}$ | $9 \times 10^{-4}$ | 0.0027 |
| 2 | $5 \times 10^{-4}$ | 0.016 | 0.077 | 0.0935 |
| 3 | $1.56 \times 10^{-5}$ | 0.0625 | 0.14 | 0.202 |
| 4 | 0.132 | 0.44 | 0.0336 | 0.6056 |
| 5 | $1.64 \times 10^{-4}$ | 0.069 | 1.377 | 1.45 |
| 6 | $3.88 \times 10^{-3}$ | $5.93 \times 10^{-4}$ | $3.04 \times 10^{-3}$ | 0.0075 |
| Library 3.15 | | | | |
| 1 | $9.5 \times 10^{-4}$ | $9.5 \times 10^{-4}$ | $9.5 \times 10^{-4}$ | 0.00285 |
| 2 | $5 \times 10^{-4}$ | 20 | 10 | 30.0 |
| 3 | $2.5 \times 10^{-5}$ | $1.35 \times 10^{-3}$ | 15 | 15.0 |
| 4 | 0.207 | 0.048 | 0.82 | 1.075 |
| 5 | $2 \times 10^{-4}$ | 0.21 | 2.875 | 3.09 |
| 6 | $1.17 \times 10^{-5}$ | 19.2 | 6.4 | 25.6 |
| Library L8.15 | | | | |
| 1 | 0.02 | 0.02 | 0.02 | 0.02 |
| 2 | $5 \times 10^{-4}$ | 0.5 | 0.018 | 0.5185 |
| 3 | $1.4 \times 10^{-3}$ | 0.077 | 1.57 | 1.6484 |
| 4 | $2.84 \times 10^{-4}$ | $5.39 \times 10^{-3}$ | 0.14 | 0.1456 |
| 5 | $2.44 \times 10^{-4}$ | 0.097 | 1.805 | 1.902 |
| 6 | 0.0142 | 70.5 | 38 | 108 |
| Library fUSE2 control in Caco-2 cells: | | | | |
| 1 | 0.02 | 0.02 | 0.02 | 0.02 |
| 2 | $5 \times 10^{-4}$ | $5 \times 10^{-4}$ | 0.03 | 0.031 |
| 3 | $2.08 \times 10^{-5}$ | $2.08 \times 10^{-5}$ | $1.125 \times 10^{-3}$ | 0.001145 |
| 4 | $5 \times 10^{-4}$ (?) | $5 \times 10^{-4}$ (?) | $5 \times 10^{-4}$ (?) | 0.0005 |
| 5 | $2.34 \times 10^{-3}$ | 0.117 | 0.025 | 0.14 |
| 6 | 9.39 | 52.5 | 94 | 155.89 |

TABLE 2

% YIELD OF φ IN T-84 CELLS

| | Time (Hours) | | | |
|---|---|---|---|---|
| Round | 1 | 5 | 24 | Total |
| Library L3.6 | | | | |
| 1 | $3.33 \times 10^{-6}$ | $1.66 \times 10^{-6}$ | 2.4 | 2.4 |
| 2 | $7.9 \times 10^{-3}$ | 0.277 | 39.68 | 39.957 |
| 3 | $9.8 \times 10^{-5}$ | $9.8 \times 10^{-5}$ | 1.04 | 1.04 |
| 4 | 0.0274 | 0.22 | 1.05 | 1.30 |
| Library L3.15 | | | | |
| 1 | $4.08 \times 10^{-4}$ | $5.8 \times 10^{-3}$ | 0.016 | 0.0218 |
| 2 | 0.342 | 0.054 | 1.78 | 2.176 |
| 3(*) | $4.3 \times 10^{-4}$ | $4.3 \times 10^{-4}$ | 2.28 | 2.28 |
| 4 | 0.00 | 8.62 | 6.7 | 15.32 |
| Library L8.15 | | | | |
| 1 | $2.7 \times 10^{-6}$ | $2.7 \times 10^{-6}$ | $2.9 \times 10^{-4}$ | 0.00029 |
| 2 | $2.6 \times 10^{-4}$ | 0.36 | 13.02 | 13.38 |
| 3 | $1.06 \times 10^{-4}$ | $1.06 \times 10^{-4}$ | 0.57 | 0.57 |
| 4 | $4.495 \times 10^{-3}$ | 52.9 | 40.2 | 93.1 |
| Library fuSE2 (control) in T-84 cells | | | | |
| 1 | $1 \times 10^{-3}$ | $1 \times 10^{-3}$ | $1 \times 10^{-3}$ | 0.001 |
| 2 | | | | |
| 3 | $2.35 \times 10^{-4}$ | 0.046 | 7.6(*) | 7.6(*) |

TABLE 2-continued

% YIELD OF φ IN T-84 CELLS

| | | Time (Hours) | | |
|---|---|---|---|---|
| Round | 1 | 5 | 24 | Total |
| 4 | 4.00 | 1.404 | 0.634 | 6.038 |
| 5 | | | | $2.4 \times 10^{-4}/3 \times 10^{-4}$ |

TABLE 3

% YIELD OF φ IN ISOLATED COLON SEGMENTS

| | | % yield | |
|---|---|---|---|
| Cycle | Time (h) | Chamber A | Chamber B |
| 1 | 1 | $4.1 \times 10^{-6}$ | $4.1 \times 10^{-6}$ |
| | 2 | 0 | $8.2 \times 10^{-6}$ |
| | 3 | 0 | $4.1 \times 10^{-6}$ |
| | 4 | 0 | 0 |
| | | Total: $4.1 \times 10^{-6}$ | Total: $1.6 \times 10^{-5}$ |
| 2 | 1 | $2.6 \times 10^{-6}$ | $2.3 \times 10^{-6}$ |
| | 2 | 0 | 0 |
| | 3 | 0 | 0 |
| | 4 | 0 | $2.3 \times 10^{-6}$ |
| | | Total: $2.6 \times 10^{-6}$ | Total: $4.6 \times 10^{-6}$ |
| 3 | 1 | $1.4 \times 10^{-4}$ | $2.5 \times 10^{-4}$ |
| | 2 | $8.5 \times 10^{-5}$ | $4.2 \times 10^{-4}$ |
| | 3 | $7.5 \times 10^{-5}$ | $6.4 \times 10^{-4}$ |
| | 4 | $7.5 \times 10^{-5}$ | $6.5 \times 10^{-4}$ |
| | | Total: $3.7 \times 10^{-4}$ | Total: $2.0 \times 10^{-3}$ |
| 4 | 1 | 0 | 0 |
| | 2 | 0 | 0 |
| | 3 | 0 | $1.2 \times 10^{-5}$ |
| | 4 | 0 | 0 |
| | | Total: 0 | Total: $1.2 \times 10^{-5}$ |
| 5 | 1 | $2.3 \times 10^{-4}$ | $2.1 \times 10^{-3}$ |
| | 2 | 4.725 | 0.049 |
| | 3 | $1.7 \times 10^{-3}$ | $1.6 \times 10^{-5}$ |
| | 4 | 0.0675 | $4.2 \times 10^{-5}$ |
| | | Total: 4.79 | Total: 0.051 |
| 6 | 1 | $7 \times 10^{-3}$ | 0.024 |
| | 2 | $2.8 \times 10^{-3}$ | 0.03 |
| | 3 | $7.5 \times 10^{-3}$ | 0.056 |
| | 4 | $5.6 \times 10^{-3}$ | 0.048 |
| | | Total: 0.023 | Total: 0.16 |

EXAMPLE 4

Identification of Peptide Sequences from Transported Phage in Colon Tissue segments Thirty-six clones from randomly selected phages from the sixth cycle of screening in rat colon segments (as given in Example 3 and Table 3) were sequenced using either the gene VIII DNA sequencing primer ELN71 (SEQ ID NO:1) or the gene III DNA sequencing primer ELN77a (SEQ ID NO:17), $^{35}$S-DATP and the Sequenase version 2.0 DNA sequencing kit (Amersham Life Science, UK). Progressing from cycle 1 to cycle 6, there is a bias in the selection of phage with random peptides coded by gene VIII as opposed to gene III, perhaps because the gene III coded peptides are present between 3–5 copies/phage particle whereas the synthetic gene VIII coded peptides are present at around 300 copies per phage particle. This higher expression level may provide a valency effect and increase the possibility of interaction with a receptor site/pathway in the tissue sample.

A number of clones/DNA sequences are present more than once, suggesting some type of preferential selection. Thus, SEQ ID NO: 2 (a Class of 9 clones—25% presence), SEQ ID NO: 3 (a Class of 5 clones—13.9% presence), SEQ ID NO: 4 (a Class of 3—8.3% presence) were determined from this 36 clone sample from cycle 6. All of these Classes consist of clones with triple DNA inserts. Individual isolates are given by SEQ. ID. NO: 5 to SEQ ID NO: 9 (triple DNA inserts) and SEQ ID NO: 10 (single insert).

Based on the recurrent random peptide sequences in these classes, two synthetic oligonucleotides were constructed and used to screen phage populations representing colon screening cycles 1–6 in a series of oligonucleotide hybridization reactions to determine whether these phage and corresponding peptides were being selected during the screening process. Thus, oligonucleotides ELN93 and ELN94 correspond to a partial coding region in those phage clones for SEQ ID NO: 2 and SEQ ID NO: 3, respectively. The incidence of reactivity per screening cycle is summarized in Table 4 below. From the data presented in Table 4, it appears that there is a gradual selection of phage which hybridize to oligonucleotide ELN93 and ELN94 progressing from cycle 1 through cycle 6. Probe reactivity is expressed as a percentage of the total number of colonies screened per phage population. As a control, the unselected, starting libraries (L3.6, L3.15 and L8.15) were also included.

TABLE 4

HYBRIDIZATION OF PHAGE POPULATIONS (COLON SCREENING CYCLES 1–6 AND UNSELECTED LIBRARIES L3.6, L3.15 AND L8.15) WITH OLIGONUCLEOTIDES ELN93 AND ELN94

| | ELN93 | ELN94 |
|---|---|---|
| 1 | 0.4 | 0.4 |
| 2 | 4.7 | 0 |
| 3 | 17.4 | 0 |
| 4 | 26.4 | 1.2 |
| 5 | >20.0 | >40.0 |
| 6 | 62.5 | >40.0 |
| L3.6 | 0.8 | 0 |
| L3.15 | 0.8 | 0 |
| L8.15 | 0.3 | 0 |

The phage populations representing Caco-2 screening cycles 1–6 and T-84 screening cycles 1–4, as given above in Example 1, Table 1 and Example 2, Table 2, respectively, were also assessed for reactivity to the oligonucleotide probes ELN93 and ELN94. The incidence of reactivity per screening cycle in Caco-2 and T-84 cells is compared to reactivity in colon tissue in Table 5 (ELN93) and Table 6 (ELN94). In these Tables, probe reactivity is expressed as a percentage of the total number of colonies screened per phage population. Some reactivity was detected in Caco-2 selected clones using ELN93. The gradual selection of ELN93 reactive phage during progression from cycles 1 to 6 observed for phage library L3.15B correlated with the pattern of reactivity previously observed for colon-selected phage although the overall reactivity achieved was substantially lower. ELN94 reactivity was identified in both Caco-2 and T-84 selected clones. Increasing reactivity from cycles 1 to 6 was observed for Caco-2 selected libraries L3.6B, L3.15B and L8.15B as well as the T-84 selected library L3.15A. The reactivity of the Caco-2 selected libraries L3.6B and L8.15B at cycle 5 (33.3% and 42.3%, respectively) was remarkably similar to that of colon A selected phage (46.0%).

TABLE 5

HYBRIDISATION OF PHAGE POPULATIONS WITH
OLIGONUCLEOTIDE ELN93
Table 5.a: Caco2 screening cycles 1–6, colon screening cycles 1–6 &
T-84 screening cycles 1–6
Table 5.b: Unselected libraries L3.6, L3.15 & L8.15

TABLE 5.a

| Cycle | Caco2 3.6A | Caco2 3.6B | Caco2 3.15A | Caco2 3.15B | Caco2 8.15A | Caco2 8.15B | Colon A | Colon B |
|---|---|---|---|---|---|---|---|---|
| 1 | 0 | 0.3 | 0 | 0 | 0 | 0 | 0.4 | NA |
| 2 | 0 | 0.3 | 0 | 0.4 | 0.3 | 1.0 | 4.7 | NA |
| 3 | 0 | 0 | 0 | 0.8 | 0 | 0 | 17.4 | NA |
| 4 | 0 | 0 | 0 | 1.2 | 0.3 | 0 | 26.4 | NA |
| 5 | 0 | 0 | 0 | 7.2 | 0 | 4.9 | >20.0 | NA |
| 6 | NA | NA | NA | NA | NA | NA | 62.5[1] (0.8)[2] | 0.6 |

| Cycle | T-84 3.6A | T-84 3.6B | T-84 3.15A | T-84 3.15B | T-84 8.15A | T-84 8.15B |
|---|---|---|---|---|---|---|
| 1 | NA | NA | NA | NA | NA | NA |
| 2 | 0 | 0 | 0 | 0 | 0 | 0 |
| 3 | 0 | 0 | 0 | 0 | 0 | 0 |
| 4 | 0 | 0 | 0 | 0 | 0 | 0 |
| 5 | NA | NA | NA | NA | NA | NA |
| 6 | 0 | 0 | 0 | 0 | 0 | 0 |

Table 5.b

| Unselected libraries | ELN93 |
|---|---|
| L3.6 | 0.8 |
| L3.15 | 0.8 |
| L8.15 | 0.3 |

[1]Assay 1
[2]Assay 2
NA Not assayed

TABLE 5.b

| Unselected libraries | ELN93 |
|---|---|
| L3.6 | 0.8 |
| L3.15 | 0.8 |
| L8.15 | 0.3 |

TABLE 6

Hybridization of phage populations with oligonucleotide ELN94
Table 6.a: Caco-2 screening cycles 1–6, colon screening cycles
1–6 & T-84 screening cycles 1–6
Table 6.b: Unselected libraries L3.6, L3.15 & L8.15

Table 6.a

| Cycle | Caco2 L3.6A | Caco2 L3.6B | Caco2 3.15A | Caco2 3.15B | Caco2 8.15A | Caco2 8.15B | Colon A | Colon B |
|---|---|---|---|---|---|---|---|---|
| 1 | 0 | 0 | 0 | 0 | 0 | 0 | 0.4 | NA |
| 2 | 0 | 0.3 | 0 | 0 | 0 | 0 | 0 | NA |
| 3 | 0 | 0 | 0 | 0 | 0 | 1.4 | 0 | NA |
| 4 | 0 | 6.0 | 0 | 1.6 | 0(3.8) | 12.9 | 1.2 | NA |
| 5 | 3.3 | >33.3 | 3.3 | 6.0 | 4.0 | 42.3 | >40.0 | NA |
| 6 | NA | NA | NA | NA | NA | NA | 46.0 | 26.2 |

| Cycle | T-84 3.6A | T-84 3.6B | T-84 3.15A | T-84 3.15B | T-84 8.15A | T-84 8.15B |
|---|---|---|---|---|---|---|
| 1 | NA | NA | NA | NA | NA | NA |

TABLE 6-continued

Hybridization of phage populations with oligonucleotide ELN94
Table 6.a: Caco-2 screening cycles 1–6, colon screening cycles
1–6 & T-84 screening cycles 1–6
Table 6.b: Unselected libraries L3.6, L3.15 & L8.15

| 2 | 0 | 0 | 0 | 0.4 | 0 | 0.4 |
|---|---|---|---|---|---|---|
| 3 | 0 | 0 | 2.8 | 0 | 0 | 2.8 |
| 4 | 4.0 | 0 | 12.8 | 4.4 | 0 | 0.4 |
| 5 | NA | NA | NA | NA | NA | NA |
| 6 | 0.4 | 0 | 0 | 0 | 0 | 0 |

Table 6.b

| Unselected libraries | ELN94 |
|---|---|
| L3.6 | 0 |
| L3.15 | 0 |
| L8.15 | 0 |

NA Not assayed

TABLE 6.b

| Unselected libraries | ELN94 |
|---|---|
| L3.6 | 0 |
| L3.15 | 0 |
| L8.15 | 0 |

EXAMPLE 5

Identification of Peptide Sequences from
Transported Phage across Caco-2 Tissue Samples Caco-2 snapwells were prepared as described above and the X30 library was screened using Caco-2 cells according to the procedures given above. FIG. 1 summarizes phage yield (% phage transported from the apical to basolateral medium) at cycles 1, 2, 3 and 4 in the basolateral medium of polarized Caco-2 cells grown on snapwells. At each cycle the basolateral medium was sampled both 1 hour and 24 hour post addition of phage to the apical medium. Thus, following addition of the initial phage library at cycle one, the basolateral medium was removed after one hour and replaced with fresh basolateral medium. Subsequently, the basolateral medium was removed 24 hours post addition of the initial phage library. In each case (one hour and 24 hour basolateral medium samples), the phage present was quantitated by titering a sample of each basolateral medium in *Escherichia coli* K91 Kan strain. The remaining basolateral medium from the one hour and twenty four hour sampling time point was combined, the phage present were PEG-precipitated, the precipitated phage was resuspended in 100 μl of TBS and was used to infect Escherichia coli K91 Kan, thus permitting amplification of the phage present in the basolateral medium as outlined previously. Following amplification, the amplified phage was titered, PEG-precipitated, resuspended in TBS and titered. The phage suspension was now ready for the next round of further selection in the cultured Caco-2 cells, by repeating the steps above using the phage transported into the basolateral medium, as outlined previously. Upon going from cycle 1 to 4, there was a 19.2 fold enrichment of phage which are transported from the apical to basolateral medium of the Caco-2 cells grown on snapwells.

Figure 2:
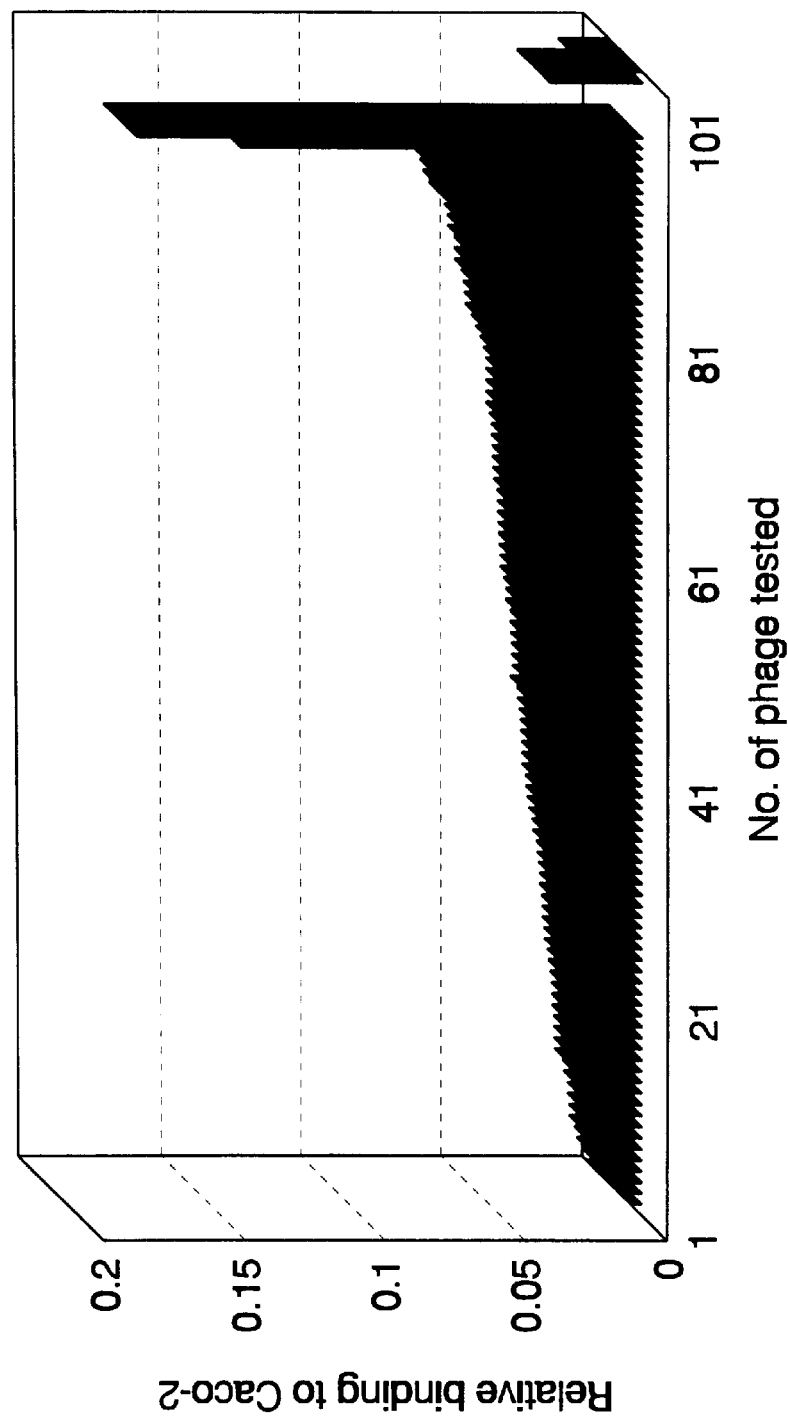
FIG. 2 shows the relative binding to fixed Caco-2 cells of 100 different phage isolates from the X30 phage display library that were obtained from the basolateral medium at completion of cycle 4 (transport from apical to the basolateral medium) panning of the X30 phage display library on Caco-2 snapwells.

FIG. 2 summarizes the relative binding of 100 different phage isolates to fixed Caco-2 cells. The 100 individual phages from the X30 library were obtained from the cycle 4 selection (transport from apical to the basolateral medium) of cultured Caco-2 cells grown on snapwells. For ELISA analysis, Caco-2 cells were grown to confluence in 96 well tissue. culture plates as described above, followed by fixing in 10% formaldehyde as described above. The ELISA analysis was performed using the HRP -anti-M13 conjugate. In this figure, the binding of each phage isolate is arranged or presented so that the "weakest" to "strongest" binding phage are presented from left to right (and not the numerical number of the phage isolate). The binding of the negative control phage (M13mp18) and the absorbance readings obtained with untreated fixed Caco-2 cells is shown on the extreme right of FIG. 3, respectively.

Figure 3:
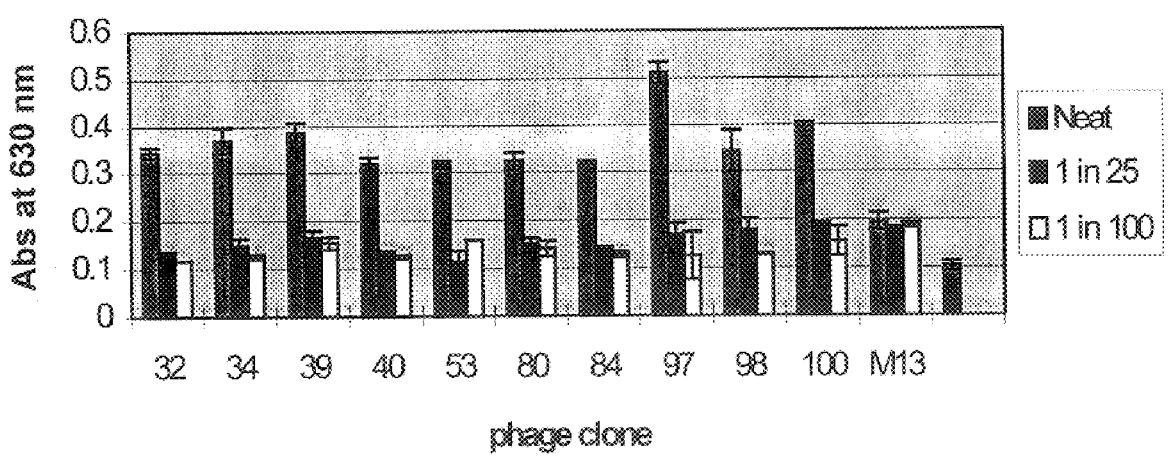
FIG. 3 shows the binding of the negative control phage M13mp18 and the top ten binders, clones 32, 34, 39, 40, 53, 80, 84, 97, 98 and 100, [each at neat, 1:25 and 1:100 dilutions] obtained from the X30 library following cycle 4 selection on Caco-2 snapwells to fixed Caco-2 cells. For reference, the ELISA absorbance reading obtained with fixed Caco-2 cells which were not treated with phage is included.
Figure 4:
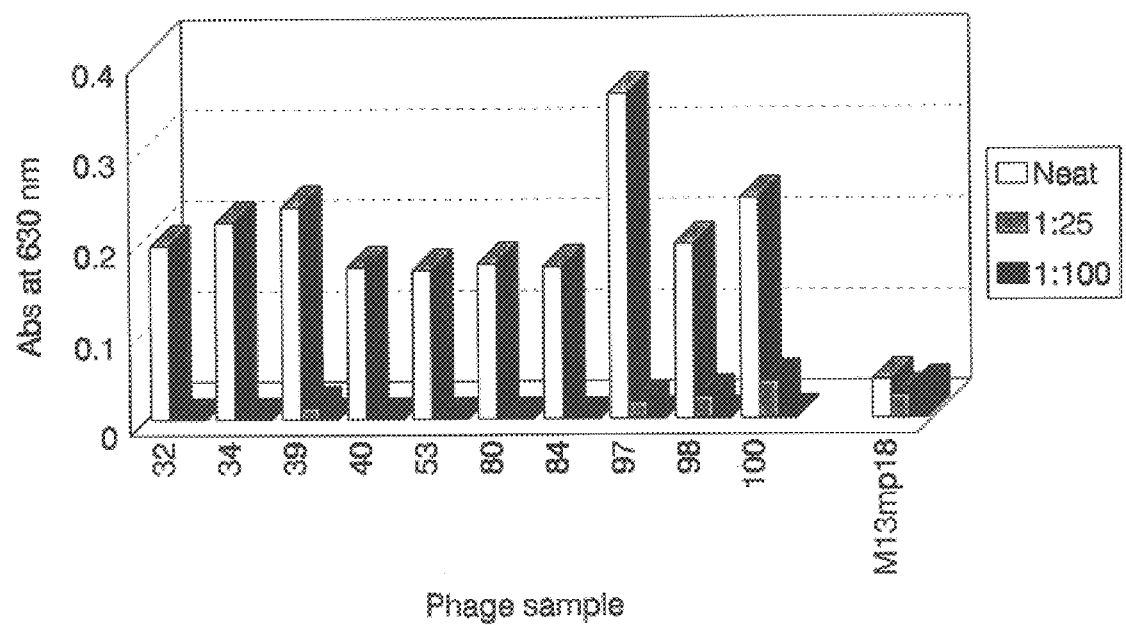
FIG. 4 shows the binding of the negative control phage M13mp18 and the top ten binders, clones 32, 34, 39, 40, 53, 80, 84, 97, 98 and 100, [each at neat, 1:25 and 1:100 dilutions] obtained from the X30 library following cycle 4 selection on Caco-2 snapwells to fixed Caco-2 cells, but where the background absorbance reading obtained from the fixed Caco-2 cells only, to which no phage was added, has been subtracted.

FIG. 3 summarizes the binding of the top ten binders, clones 32, 34, 39, 40, 53, 80, 84, 97, 98, and 100 to fixed Caco-2 cells, along with binding of the negative control phage M13mp18 to the fixed Caco-2 cells, with phage binding monitored by ELISA analysis as described above. The binding studies were performed in duplicate, using neat phage (~$10^{10}$ pfu/ml) or diluted phage samples (diluted 1:25 and 1:100 in each case). As a control, the absorbance readings obtained using the fixed Caco-2 cells in which no phage was added, is shown on the right hand side of FIG. 3. FIG. 4 is essentially the same as FIG. 3, except that the background absorbance readings obtained using the fixed Caco-2 cells only, to which no phage was added, has been subtracted from the absorbance readings obtained using fixed Caco-2 cells which were incubated with the indicated phage clone samples and the negative control phage M13mp18. The precise titers of neat phage used for each clone are given in Table 7.

TABLE 7

TITERS OF NEAT PHAGE SAMPLES FOR THE TOP TEN BINDERS

| CLONE | pfu/ml |
|---|---|
| 32 | $1.19 \times 10^{10}$ |
| 34 | $2.87 \times 10^{10}$ |
| 39 | $1.34 \times 10^{10}$ |
| 40 | $9.09 \times 10^{9}$ |
| 53 | $1.89 \times 10^{10}$ |

TABLE 7-continued

TITERS OF NEAT PHAGE SAMPLES FOR THE TOP TEN BINDERS

| CLONE | pfu/ml |
|---|---|
| 80 | $2.25 \times 10^{10}$ |
| 84 | $1.27 \times 10^{10}$ |
| 87 | $7.99 \times 10^{9}$ |
| 98 | $1.99 \times 10^{10}$ |
| 100 | $8.36 \times 10^{9}$ |

Figure 5:
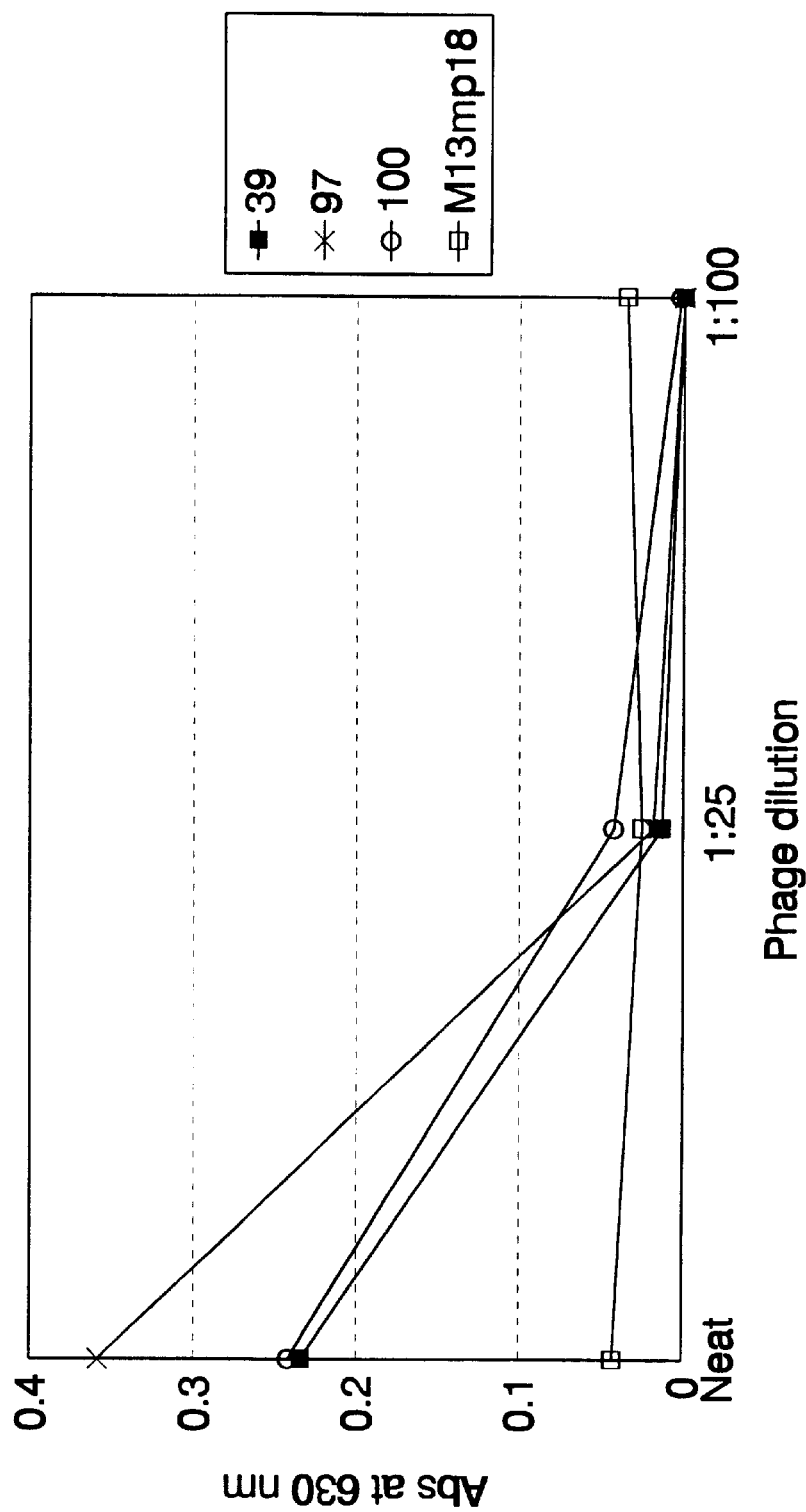
FIG. 5 is a graphical representation of the binding of the phage clones 39, 97 and 100 and the negative control phage M13mp18, using either neat phage samples or the same phage diluted 1:25 and 1:100, to fixed Caco-2 cells.

FIG. 5 is a graphical representation of the binding of the phage clones 39, 97 and 100 and the negative control phage M13mp18, to fixed Caco-2 cells using either neat phage sample (at ~$10^{10}$ pfu/ml) or the same phage diluted 1:25 and 1:100. The phage binding experiments and subsequent ELISA analysis was performed as previously outlined. This data shows that the phage clones 39, 97 and 100 bind in a dose response manner, with reduction in the ELISA absorbance readings obtained following dilution of the phage either 1:25 or 1:100. In contrast, the negative control phage M13mp18 does not bind in a dose response manner, with linear absorbance readings obtained using either neat, 1:25 or 1:100 diluted phage.

The top ten binders, clones 32, 34, 39, 40, 53, 80, 84, 97, 98 and 100 were sequenced using procedures outlined above. Eight of these sequences were identical to the sequence of clone 97 giving DNA sequence SEQ. NO. ID: 11 and peptide sequence SEQ. NO. ID: 12. The two remaining clones (53 and 100) produced individual isolates DNA SEQ. NOS. ID: 13 and 15 with the corresponding peptide sequences SEQ. NOS. ID: 14 and 16, respectively. One skilled in the art could determine without undue experimentation which fragments of these peptides permit or facilitate the transport of an active agnet through a human or animal tissue. On the basis of the results of Example 4, it is expected that these fragments consist of at least 6 amino acid residues.

EXAMPLE 6

Transport of Phage from Rat Lumen into the Portal and Systemic Circulation

In this study, phage from random phage display libraries as well as control phage were injected into the lumen of the rat gastrointestinal tract (in situ rat closed loop model). Blood was collected over time from either the systemic circulation or portal circulation and the number of phage which were transported to the circulation was determined by titering blood samples in E. coli.

The phage display libraries used in this study were D38 and DC43 in which gene III codes for random 38-mer and 43-mer peptides, respectively. As a negative control, the identical phage M13mp 18, in which gene III does not code for a "random" peptide sequence, was used. Both the library phages D38 and DC43 were prepared from E.coli, mixed together, dialyzed against PBS, precipitated using PEG/NaCl and were resuspended in PBS buffer. The M13mp18 control was processed in a similar manner. The titer of each phage Approximately 0.4 ml of the blood was collected at each time point in each model system. 30 μl of the collected blood (systemic) was mixed with 100 μl of the prepared E.coli strain K91Kan, incubated at 37° C. for 30 min, and plated out for plaque formation using Top Agarose on LB plates. Various negative controls were included in the titering experiments. The following day the number of plaques forming units (pfu's) was determined. Similarly, 30 μl of the collected blood (portal) and serial dilutions (1:100, 1:1000) thereof was mixed with 100 μl of the prepared E. coli strain K91 Kan, incubated at 37° C. for 30 min, and plated out for plaque formation using Top Agarose on LB plates. The following day the number of plaques forming units (pfu's) was determined.

In addition, approximately 300 μl of the collected blood from each time point (systemic and portal) was incubated with 5 ml of prepared E.coli strain K91Kan in modified growth media containing 5 mM $MgCl_2$/MgSO4, incubated at 37° C. overnight with shaking (to permit phage amplification). The samples were centrifuged and the cell pellet was discarded. Samples of the phage supernatant were collected, serially diluted ($10^{-2}$, $10^{-4}$, $10^{-6}$, $10^{-8}$) in TBS buffer and were plated for plaques in order to determine the number of pfu's present in the amplified phage samples.

Furthermore, an aliquot of phage was removed from the "amplified" supernatants obtained from test animals #R4–R7 (samples from each time point were used), combined and was PEG-precipitated for two hours. The precipitated phage was resuspended in PBS buffer and was injected into closed loop model of animal #R15, followed by portal sampling.

The number of phage transported from the closed loop model into the systemic circulation is presented in Table 8. The number of phage transported from the closed loop model into the portal circulation is presented in Table 9. These numbers are corrected for phage input difference and for volume input differences. Clearly, more phage are present in the portal samples than in the systemic samples, indicative of either hepatic or RES clearance and/or phage instability in the systemic circulation. In addition, the uptake of phage from the GIT into the portal circulation is quite rapid, with substantial number of phages detected within 15 minutes. The results from the portal sampling experiments would also indicate that the kinetics of uptake of phage from the D38/DC43 libraries is quicker than that of the control phage. Thus, there may be preferential uptake of phage coding for random peptide sequences from the GIT into the portal circulation. In the case of animals R13, R14 and R15*, the % of the phage transported into the titered blood sample within the limited time frame (30, 45 and 15 mins, respectively) is estimated as 0.13%, 1.1% and 3%, respectively.

TABLE 8

NUMBER OF PHAGE TRANSPORTED FROM THE CLOSED LOOP MODEL INTO THE SYSTEMIC CIRCULATION

| Time (min) | R1 | R2 | R3 | R4 | R5 | R6 | R7 |
|---|---|---|---|---|---|---|---|
| 0 | 0 | 0 | 0 | 0 | 0 | 0 | 0 |
| 15 | 0 | 1 | 9 | 0 | 0 | 1 | 7 |
| 30 | 2 | 1 | 0 | 0 | 46 | 1 | 11 |
| 45 | 10 | 4 | 2 | 1 | 32 | 0 | 20 |
| 60 | 63 | 19 | 21 | 1 | 114 | 0 | 21 |
| 90 | 104 | 20 | 18 | 3 | 115 | 0 | 22 |
| 120 | 94 | 24 | 27 | 0 | 64 | 0 | 6 |
| 180 | 94 | 12 | 23 | 1 | 413 | 0 | 0 |
| 240 | 14 | 1 | 20 | 0 | 36 | 0 | 0 |
| 300 | 1 | 1 | 4 | 2 | 0 | 0 | 0 |
| Total number of transported phage | 382 | 83 | 124 | 8 | 820 | 2 | 87 |

Animals R1, R2 and R3 received the control phage M13mp18
Animals R4, R5, R6 and R7 received the test phage D38/DC43 mix

TABLE 9

NUMBER OF PHAGE TRANSPORTED FROM THE CLOSED LOOP MODEL INTO THE PORTAL CIRCULATION

| Time (min) | R8 | R9 | R10 | R11 | R12 | R13 | R14 | R15* |
|---|---|---|---|---|---|---|---|---|
| 15 | 15 | 6 | 3 | 1 | 19 | 231,000 | 1,000,000 | 20,000 |
| 30 | 1 | 5 | 26 | — | 0 | 60,000 | 272,000 | — |
| 45 | — | 1 | 555 | — | 1 | — | 1,240,000 | — |
| 60 | — | — | — | — | 420,000 | — | — | — |

Animals R8, R9 and R10 received the control phage M13mp18
Animals R11, R12, R13 and R14 received the test phage D38/DC43 mix
Animal R15* received the combined phage samples from animals R4–R7 (see Table 8) which were sampled from the systemic circulation on day one, followed by PEG precipitation and resuspension in PBS. On subsequent analysis, the titer of this phage was found to be 100 times greater than the other phage samples used for animals R8–R14. Thus, the date presented for animal R15* in Table 9 is adjusted down.

These studies demonstrate that both the control phage and the D38/DC43 phages are transported over time from the lumen of the GIT into the portal and systemic circulation, as demonstrated by titering the phage transported to the blood in E.coli. More phage are transported from the test phage samples into the portal circulation than the corresponding control phage sample. In addition, the kinetics of transport of the test phage into the portal circulation does appear to exceed that of the control phage. Phage from the D38/DC43 libraries which appeared in the systemic circulation of different animals (R4–R7) were pooled, amplified in E.coli, precipitated, and re-applied to the lumen of the GIT, followed by collection in the portal circulation and titering in E.coli. These selected phage were also transported from the lumen of the GIT into the portal circulation. This in situ loop model may represent an attractive screening model in which to identify peptide sequences which facilitate transport of phage and particles from the GIT into the circulation.

Using this screening model system, a number of preselected phage libraries now exist. These are the one pass systemic phage library from animals R4–R7, a one-pass portal library from animals R11–R14 and the two pass, rapid transport, systemic-portal phage library SP-2 from animal R15*.

EXAMPLE 7

Transport of Phage from Preselected Phage Libraries from the Rat Lumen into the Portal and Systemic Circulation Four preselected phage libraries, GI-D, GI-S, GI-H and GI-P, are constructed by pooling phage previously selected by screening random phage display libraries D38 and DC43 using four distinct receptor or binding sites located in the GIT. Similar to Example 7 above, these preselected phage libraries together with the negative control phage M13mp18 are injected into the rat closed loop model (6 animals per preselected phage library), blood is collected over time from the portal circulation via the portal vein and, at the termination of the experiment, a systemic blood sample is collected from the tail vein and the intestinal tissue region from the closed loop is collected.

In particular, phages selected in vitro to each receptor or binding site located in the GIT were amplified in E. coli, PEG-precipitated, resuspended in TBS and the titer of each phage sample was determined by plaquing in E.coli as described above. Subsequently, an equal number of each phage ($8 \times 10^8$ phage) for each receptor site was pooled into a preselected phage library together with the negative control phage M13mp18 and each preselected phage library was administered to 6 Wistar rats per library (rats 1–6; GI-D, rats 7–12; GI-S, rats 13–18; GI-P, and rats 19–24; GI-H). Using the in situ loop model described above, 0.5 ml of preselected phage library solution was injected into the tied-off portion of the duodenum/jejunum. Blood was collected into heparinised tubes from the portal vein at 0, 15, 30, 45 and 60 minutes. A blood sample was taken from systemic circulation at the end of the experiment. Similarly, the portion of the duodenum/jejunum used for phage injection was taken at the end of the experiment.

30 $\mu$l of the collected portal blood (neat and $10^{-2}$, $10^{-4}$, $10^{-6}$ dilutions) was added to 30 $\mu$l E.coli K91Kan cells (overnight culture) and incubated at 37° C. for 10 min. Subsequently, 3 ml of top agarose was added and the samples were plated for plaques. 100 $\mu$l of the collected portal blood was added to 100 $\mu$l of E.coli K91 Kan. 5 ml of LB medium was then added and the samples were incubated at 37° C. overnight in a rotating microbial incubator. The E.coli was removed by centrifugation and the amplified phage supernatant samples were either titered directly or were PEG-precipitated, resuspended in TBS and titered. Following titration of the amplified phage, samples containing phage from each set of animals were combined, adjusting the titer of each sample to the same titer, and were plated for plaques on LB agar plates (22 cm$^2$ square plates). Either 12,000 or 24,000 phage were plated for plaques.

30 $\mu$l of the collected systemic blood (neat and $10^{-2}$, $10^{-4}$, $10^{-6}$ dilutions) was added to E. coli K91Kan cells, incubated at 37° C. for 10 min. Three ml of top agarose was then added and the samples were plated for plaques. 100 $\mu$l of the collected systemic blood was added to 100 $\mu$l of E.coli K91 Kan, incubated at 37° C. for 10 min. 5 ml of LB medium was then added and the samples were incubated at 37° C. overnight in a rotating microbial incubator. The E.coli was removed by centrifugation and the amplified phage supernatant samples were either titered directly or were PEG-precipitated, resuspended in TBS and titered. Following titration of the amplified phage, samples containing phage from each set of animals were combined, adjusting the titer of each sample to the same titer, and were plated for plaques on LB agar plates (22 cm$^2$ square plates). Either 12,000 or 24,000 phage were plated for plaques.

The intestinal tissue portion used in each closed loop was excised. The tissue was cut into small segments, followed by 3 washings in sterile PBS containing protease inhibitors, and homogenized in an Ultra thorex homogeniser (Int-D samples). Alternatively, the tissue (in PBS supplemented with protease inhibitors) was homogenized in an Ultra Thorex homogeniser, washed 3 times in PBS containing protease inhibitors and resuspended in PBS containing protease inhibitors (Int-G samples). In each case, serial dilutions (neat and $10^{-2}$, $10^{-4}$, $10^{-6}$ dilutions) of the tissue homogenate was titered in E. coli. In addition, an aliquot (100 $\mu$l) of the tissue homogenate was added to 100 $\mu$l of E.coli K91 Kan, incubated at 37° C. for 10 min, followed by addition of 5 ml of LB medium and incubation overnight at 37° C. in a rotating microbial incubator.

The phage amplified from the portal blood, systemic blood and intestinal tissue was plated for plaques. The plaques were transferred to Hybond-N Nylon filters, followed by denaturation (1.5M NaCl, 0.5M NaOH), neutral ization (0.5M TRIS-HCl, pH7.4, 1.5M NaCl), washing in 2×SSC buffer. The filters were air-dried, and the DNA was cross-linked to the filter (UV crosslinking: 2 min, high setting). The filters were incubated in pre-hybridization buffer (6×SSC, 5×Denhardt's solution, 0.1% SDS, 20 μg/ml yeast tRNA) at 40° C.–45° C. for at least 60 min.

conditions used the oligonucleotides essentially did not hybridise to the negative control phage template M13mp18. Two oligonucleotides were synthesised to the phage M13mp18–(1) a positive oligonucleotide which hybridises to a conserved sequence in both M13mp18 and each of the GIT receptor or GIT binding site selected phages

TABLE 10

SUMMARY OF HYBRIDIZATION RESULTS

| Phage | Portal | Int.-G | Int.-D | Phage | Int-G | Portal | Systemic |
|---|---|---|---|---|---|---|---|
| A: (GI-S) | | | | C: (GI-H) | | | |
| S15 | ++ | +/– | +/– | H40 | – | – | ++++ |
| S21 | – | – | – | HAX9 | ND | ND | ND |
| S22 | – | –/+ | – | HAX35 | – | + | – |
| SNI-10 | +++/+ | ++ | ++ | HAX40 | – | – | – |
| SNI-28 | – | – | – | HAX42 | – | ++ | ++ |
| SNI-34 | ++ | – | – | HCA3 | – | – | – |
| SNI-38 | ++ | – | – | PAX2 | – | +++ | ++++ |
| SNI-45 | – | – | – | M13(positive) | ++++++ | ++++++ | ++++++ |
| SNIAX-2 | – | – | – | M13(negative) | – | ––/+ | – |
| SNIAX-6- | – | – | | | | | |
| SNIAX-8 | – | – | – | | | | |
| M13(positive) | ++++++ | ++++++ | ++++++ | | | | |
| M13(negative) | ND | + | – | | | | |
| B: (GI-D) | | | | D: (GI-P) | | | |
| DAB3 | +++ | +/– | –/+ | PAX2 | – | ++ | – |
| DAB7 | ++ | ++ | –/+ | PAX9 | ++ | +++ | – |
| DAB10 | ++++++ | +/– | –/+ | PAX14 | – | ++ | – |
| DAB18 | – | – | – | PAX15 | –/+ | – | – |
| DAB24 | – | – | – | PAX16 | – | – | – |
| DAB30 | ++++ | ++ | +++ | PAX17 | + | ++/+ | – |
| DAX15 | – | – | – | PAX18 | – | – | – |
| DAX23 | –/+ | + | –/+ | PAX35 | – | – | – |
| DAX24 | – | – | – | PAX38 | –/+ | – | – |
| DAX27 | – | + | – | PAX40 | + | +++ | – |
| DCX8 | +++++ | +/– | – | PAX43 | + | – | – |
| DCX11 | ++++++ | ++ | –/+ | PAX45 | – | – | – |
| DCX26 | – | – | – | PAX46 | – | +++ | – |
| DCX33 | +++ | ++ | ++ | P31 | ++ | ++++ | ++ |
| DCX36 | – | – | – | P90 | – | – | – |
| DCX39 | – | –/+ | – | 5PAX3 | ++/+ | ++ | – |
| DCX42 | – | – | –/+ | 5PAX5 | – | – | ++ |
| DCX45 | – | ++ | – | 5PAX7 | +++ | – | – |
| M13(positive) | ++++++ | ++++++ | ++++++ | 5PAX12 | ++++ | ++ | – |
| M13(negative) | +/– | –/+ | – | H40 | ++ | ++ | – |
| | | | | M13(positive) | ++++++ | ++++++ | ++++++ |
| | | | | M13(negative) | – | – | – |

Synthetic oligonucleotides, (22-mers), complimentary to regions coding for the receptor or binding sites used to create the preselected phage library, were synthesized. The oligonucleotides (5 pmol) were 5'end labelled with $^{32}$P-ATP and T4 polynucleotide kinase and approximately 2.5 pmol of labelled oligonucleotide was used in hybridization studies. Hybridization's were performed at 40–45° C. overnight in buffer containing 6×SSC, 5×Denhardt's solution, 0.1% SDS, 20 μg/ml yeast tRNA and the radiolabeled synthetic oligonucleotide, followed by washings (20–30 min at 40–45° C.) in the following buffers: (i) 2×SSC /0.1% SDS, (ii) 1×SSC /0.1% SDS, (iii) 0.1×SSC/0.1% SDS. The filters were air-dried and exposed for autoradiography for 15 hours, 24 hours or 72 hours.

Table 10 summarises the results from the hybridization studies outlined above. Apart from the synthetic oligonucleotide to HAX9, all oligonucleotides were initially confirmed to be radiolabeled, as determined by hybridisation to the corresponding phage target (eg., phage S15 hybridised to the oligonucleotide S15). In addition, under the experimental

[designated M13 (positive)] in Table 10 and (2) a negative oligonucleotide which only hybridises to a sequence unique to the multiple cloning site of phage M13mp18 and which does not hybridise to any of the GIT receptor or GIT binding site selected phages.

In the case of the GI-S pool of phages, only four phages are transported from the closed loop model into the portal circulation—phages S15, SNI-10, SNI-34 and SNI-38. The other phages, S21, S22, SNI-28, SNI-45, SNIAX-2, SNIAX-6 and SNMAX-8 are not transported from the GIT into the portal circulation. In addition, phages SNI-10 and to a lesser extent phages S15 and S22 were found in the intestine samples or fractions, whereas the other phages were not. There was a very low presence (<0.1%) of the phage M13mp18 in the Int-G samples. These results show that phages can be further selected from pre-selected libraries, permitting the identification of phages which are transported from the GIT closed loop into the portal circulation or phages which bind to or are internalised by intestinal tissue.

In the case of the GI-D pool of phages, there is a rank order by which phages are transported from the GIT closed loop model into the portal circulation, with phages DCX11 and DAB10 preferably transported, followed by phages DCX8, DAB30, DAB3 and DAB7. A number of phages from this pool are not transported into the portal circulation, including phages DAB18, DAB24, DAX15, DAX24, DAX27, DCX26, DCX36, DCX39, DCX42, DCX45. There is a very low level of transport of phage DAX23 from the GIT into the portal circulation. Similarly, only some of the phages are found in the intestinal samples fractions, including phages DAB30, DCX33, DAB7, DCX11, DCX45 and to a much lesser extent phages DAB3, DAB10, DCX8, DCX39, DCX42. Some phages are not found in the intestinal samples, including phages DAB18, DAB24, DAX15, DAX24, DCX26, and DCX36. There was a very low presence (<0.1%) of the phage M13mp18 in the Int-G samples. These results show that phages can be further selected from pre-selected libraries, permitting the identification of phages which are transported from the GIT closed loop into the portal circulation or phages which bind to or are internalised by intestinal tissue.

In the case of the GI-H pool of phages, there is a rank order by which phages are transported from the GIT closed loop model into the portal or systemic circulation, with phages PAX2 (which was used at a 4×concentration relative to the other phages in this pool) followed by phage HAX42 found in the portal and systemic circulation and phage H40 found in the systemic circulation only. None of the phages in this pool were found in the intestine samples or fractions. Phage M13mp18 was not found in the intestine fractions or systemic circulation, with very low incidence (<0.001%) in the portal circulation. These results show that phages can be further selected from pre-selected libraries, permitting the identification of phages which are transported from the GIT closed loop into the portal and/or systemic circulation or phages which bind to or are internalised by intestinal tissue.

In the case of the GI-P pool of phages, the phages PAX2 and H40 were also included in this pool. A number of phages from this pool were found in the portal circulation, including phages P31, PAX46, PAX9, H40, PAX17, PAX40, PAX2, PAX14, 5PAX3 and 5PAX12. A number of phages were not found in the portal blood including the negative control phage M13mp18, PAX15, PAX16, PAX18, PAX35, PAX38, PAX43, PAX45, P90, 5PAX5 and 5PAX7. The only phage found in the systemic circulation were phages 5PAX5 and P31. In addition, there was preferential binding of some phages to the intestine, including phages 5PAX12, 5PAX7, 5PAX3, H40, P31, PAX9, and to a lesser extent phages PAX38 and PAX15. Some phages were not found in the intestine samples, including the negative control phage M13mp18 and the phages PAX2, PAX14, PAX16, PAX18, PAX35, PAX45, PAX46, P90 and 5PAX5. These results show that phages can be further selected from pre-selected libraries, permitting the identification of phages which are transported from the GIT closed loop into the portal and/or systemic circulation or phages which bind to or are internalised by intestinal tissue.

The present invention is not to be limited in scope by the specific embodiments described herein. Various modifications of the invention in addition to those described herein will become apparent to those skilled in the art from the foregoing description and accompanying figures. Such modifications are intended to fall within the scope of the appended claims.

What is claimed is:

1. A peptide comprising SEQ ID NO: 12 or a fragment thereof which contains at least 6 amino acid residues.

2. A peptide comprising SEQ ID NO: 14 or a fragment thereof which contains at least 6 amino acid residues.

3. A peptide comprising SEQ ID NO: 16 or a fragment thereof which contains at least 6 ammo acid residues.

4. A peptide claim 1 said peptide comprising SEQ ID NO:12.

5. A peptide claim 2 said peptide comprising SEQ ID NO:14.

6. A peptide claim 3 said peptide comprising SEQ ID NO:16.

* * * * *